(12) United States Patent
Malessa et al.

(10) Patent No.: US 9,822,243 B2
(45) Date of Patent: Nov. 21, 2017

(54) FREEZE-DRIED COMPOSITION

(75) Inventors: Ralf Malessa, Essen (DE); Karin Wiesweg, Coesfeld (DE); Claudia Elsinghorst, Billerbeck (DE)

(73) Assignee: DR. SUWELACK SKIN & HEALTH CARE AG, Billerbeck (DE)

( * ) Notice: Subject to any disclaimer, the term of this patent is extended or adjusted under 35 U.S.C. 154(b) by 218 days.

(21) Appl. No.: 12/763,687

(22) Filed: Apr. 20, 2010

(65) Prior Publication Data

US 2010/0272669 A1    Oct. 28, 2010

(30) Foreign Application Priority Data

Apr. 22, 2009   (EP) .................................... 09158478

(51) Int. Cl.
| | |
|---|---|
| C08L 5/00 | (2006.01) |
| C08L 33/02 | (2006.01) |
| C08L 5/04 | (2006.01) |
| C08L 5/08 | (2006.01) |
| C08L 99/00 | (2006.01) |
| C08L 1/00 | (2006.01) |
| A61L 15/22 | (2006.01) |
| C08L 1/28 | (2006.01) |

(52) U.S. Cl.
CPC ............... *C08L 5/00* (2013.01); *A61L 15/225* (2013.01); *C08L 1/286* (2013.01); *C08L 5/04* (2013.01); *C08L 5/08* (2013.01); *C08L 33/02* (2013.01); *C08L 99/00* (2013.01); C08L 1/00 (2013.01); C08L 2205/02 (2013.01); C08L 2205/03 (2013.01)

(58) Field of Classification Search
CPC .... C08L 5/04; C08L 1/286; C08L 5/08; C08L 5/00; C08L 33/02
See application file for complete search history.

(56) References Cited

U.S. PATENT DOCUMENTS

| | | | |
|---|---|---|---|
| 5,314,915 A * | 5/1994 | Rencher | 514/535 |
| 5,658,582 A * | 8/1997 | Dorigatti et al. | 424/402 |
| 5,744,155 A * | 4/1998 | Friedman et al. | 424/434 |
| 2004/0030283 A1 * | 2/2004 | Brooks | 604/48 |
| 2008/0152698 A1 * | 6/2008 | Effing et al. | 424/445 |

FOREIGN PATENT DOCUMENTS

| | | | |
|---|---|---|---|
| FR | WO01/82886 A1 * | 11/2001 | 424/78 |
| GB | 2080814 | 2/1982 | |
| GB | 2431104 | 4/2007 | |
| WO | 94/01468 | 1/1994 | |
| WO | 99/65538 | 12/1999 | |
| WO | 00/22083 | 4/2000 | |
| WO | 01/13967 | 3/2001 | |
| WO | 01/28600 | 4/2001 | |
| WO | 03/051412 | 6/2003 | |
| WO | 03/068843 | 8/2003 | |
| WO | 2005/123034 | 12/2005 | |
| WO | 2007/122232 | 11/2007 | |
| WO | 2008/070270 | 6/2008 | |

OTHER PUBLICATIONS

Translation of description of WO 01/82886 A1, published Nov. 8, 2011; Inventors Declomesnil, et al.*

* cited by examiner

*Primary Examiner* — Audrea Buckley
(74) *Attorney, Agent, or Firm* — Ballard Spahr LLP

(57) ABSTRACT

The invention relates to freeze-dried compositions comprising
  a) at least one polymer based on polyacrylic acids and salts thereof,
  b) at least one natural polymer,
  c) optionally at least one further polymer which differs from a) and b) and
  d) optionally one or more active compounds and/or auxiliary substances.

The invention furthermore relates to a process for the preparation of such freeze-dried compositions, the combination of such freeze-dried compositions in kit-of-parts arrangements together with aqueous solutions and the use of the freeze-dried compositions and of the kit-of-parts combinations for cosmetic and pharmaceutical use, in particular for use as a cosmetic mask or as a wound covering and for the preparation of pharmaceutical agents for treatment of dermal wounds, such as, in particular, chronic wounds, ulcus cruris or decubitus.

14 Claims, No Drawings

FREEZE-DRIED COMPOSITION

BACKGROUND OF THE INVENTION

The invention relates to freeze-dried compositions comprising
- a) at least one polymer based on polyacrylic acids and salts thereof,
- b) at least one natural polymer,
- c) optionally at least one further polymer which differs from a) and b) and
- d) optionally one or more active compounds and/or auxiliary substances.

The invention furthermore relates to a process for the preparation of such freeze-dried compositions, the combination of such freeze-dried compositions in kit-of-parts arrangements together with aqueous solutions and the use of the freeze-dried compositions and of the kit-of-parts combinations for cosmetic and pharmaceutical use, in particular for use as a cosmetic mask or as a wound covering and for the preparation of pharmaceutical agents for treatment of dermal wounds, such as, in particular, chronic wounds, ulcus cruris or decubitus.

Various agents for cosmetic and therapeutic treatment of the human and/or animal body are known in the most diverse presentation and administration forms. Compositions and agents in the form of solid, dry formulations configured as sponges, sheets, matrices, coverings, pads, leaves, masks, layers or other planar forms as well as those in the form of shaped bodies of large format play an important role here, in particular in the pharmaceutical field of wound care, but increasingly also in the field of cosmetic uses. Such embodiments are particularly suitable for external and areal treatment and care of the skin, and in particular for the care of areal skin injuries or wounds. Depending on the desired treatment aim or chosen field of use of such coverings, particular, sometimes very specific material and functional requirements are imposed on such compositions, in particular on their chemical composition and their physical or biochemical mode of action and function. Specifically in the case of external dermal treatment, the complex biochemical interactions and modes of function with the organ "skin" are to be remembered.

In this context, the care and protection of the skin, e.g. by a cosmetic treatment, and the restoration, curing or alleviation of dysfunctions or injuries of the skin by a therapeutic treatment are of virtually equal importance.

Care and preventive protection by a cosmetic treatment can be achieved in particular by application and introduction of active compounds, nutrients and/or care substances, but also by assisting or improving the physical and mechanical protection and/or barrier properties, such as elasticity, smoothness/roughness, dryness or biochemical equilibrium, of the skin. In particular, assisting, protecting, regulating and improving the moisture and fat content, in particular the so-called "natural moisturizing factor" (NMF) and the barrier function, of the skin represent an important treatment element here.

In the event of injury to or impairment of the skin or one of its central functions, treatment which is accompanied by an alleviating, healing or restoring action is of particular importance. Such a therapeutic treatment can likewise be effected by supplying particular active substances, healing substances or active compounds having a positive action, or by suitable assisting physical or biochemical methods which assist and favourably influence self-healing. The nature and scope of such a therapeutic treatment in this context depends in particular on the nature of the injury or dysfunction and is to be matched specifically to the affected layers of skin. In the field of wound care, so-called wound exudate management, wound debridement or influencing and regulation of the wound climate are to be mentioned here in particular.

For both fields, care cosmetics and the therapeutic field of skin treatment, the use of solid, dry, absorbent or hydratable formulation forms, in particular in the form of planar sheets, coverings or masks, is particularly suitable in principle and is also already widespread. In this context, those formulations which, in addition to the application of active compounds, also in themselves already have a skin-hydrating action are of interest in particular. This is equally relevant to cosmetic and to therapeutic skin treatment.

In particular, formulations based on hydrophilic, swellable hydrocolloids or polymers are known and used for this purpose. From the therapeutic field of wound treatment specifically, hydrogels in particular are known as wound treatment agents. In this context, hydrogels are distinguished in particular by a high water content or a high liquid uptake and storage capacity, as a result of which they are particularly suitable in particular for moist wound treatment. Hydrogels based on polyacrylates and their derivatives and those based on polyacrylic acids and salts thereof are particularly suitable compositions. In particular, synthetic acrylic acid polymers of the so-called "carbomers" groups are distinguished by a particularly good water uptake capacity. In this context, according to the USP-NF, British Pharmacopoeia, United States Adopted Names council (USAN) and Cosmetic Toiletries and Fragrance Association (CTFA), the term "carbomers" describes the group of Carbopols. Carbomers are also known by the term "superabsorbers".

Those substances which are capable of taking up several times their own weight—up to 1,000 times—of liquids (usually water or distilled water) are called "superabsorbers" (also: superabsorbent polymers). In chemical terms, the carbomers are complex copolymers of acrylic acid and sodium acrylate, optionally additional crosslinking agents and/or acrylic acid derivatives, it being possible for the chemical composition of carbomers to vary.

Polyacrylates, their derivatives or also carbomers, and superabsorbers have a broad use spectrum both in the cosmetic and in the medical field of use. In cosmetics, carbomers or superabsorbers are employed as viscosity-increasing components in creams and lotions, as described, for example, in DE 10195737. By increasing the viscosity in the end product, they counteract a phase separation of the lipophilic and hydrophilic phase additionally to the emulsifiers, lead to a rich texture and contribute inter alia towards a pleasant sensation on the skin after application. Pure hydrogel products with a viscosity component based only on polyacrylate, which contain no or hardly any oils and only small amount of emulsifiers, acquire their phase stability chiefly via the viscosity of the polyacrylates contained therein.

On the basis of the capacity of polyacrylates, in addition to their good viscosity-increasing properties, also of taking up extreme amounts of aqueous liquids and of storing and holding these with extreme swelling, they are employed in particular in the therapeutic field of wound care, in particular in medical products for exudate management. The polyacrylate is usually employed here in the dry state as a powder or granules.

The preparation of micro- or nanoparticles or granular materials from polyacrylic acid polymers is also known, such particles usually being prepared from mixtures of the polyacrylic acid with further stabilizing natural or semisynthetic polymers. Thus, WO 00/22083 describes nanoporous granular materials based on acrylic acid/carboxymethylcellulose solutions, and WO 05/123034 describes microparticulate systems for example based on mixtures of polymethacrylate and sodium alginate solutions, which are in each case obtained by spray misting and freeze drying the polyacrylate-polymer mixtures.

The use of polyacrylic acid polymers for the preparation of microgel particles and the use thereof for encapsulation of active compounds, for example in the form of a microgel particle suspension applied to a wound covering of oxidized cotton, is known from GB 2431104.

Wound coverings based on polyacrylic acid polymers are moreover often combined with active compounds which are said to have a positive influence on wound healing. Thus e.g. a combination with fibronectin is described in WO 01/13967 or a combination with fibrillar collagen is described in GB 2080814 or a combination with growth factors, such as VEGF and PDGF, is described in WO 08/070,270.

In addition e.g. WO 07/122,232 discloses freeze-dried compositions for wound treatment which are obtainable by extrusion or electrospinning processes from mixtures of gelatine with polyacrylic acids.

Hydrogels with polyacrylate constituents and acrylates are moreover employed as glues or adhesives in the field of therapeutic wound care agents.

Both in cosmetic and in therapeutic skin treatment, however, those formulations which, in addition to a high wetting speed and a high water uptake and retention capacity, additionally have a good moistening and skin-hydrating action, that is to say also a good water-releasing capacity, are preferably also desirable. The hydrating action in cosmetic skin treatment plays an essential role in improving the mechanical and physical nature of the skin, e.g. with respect to elasticity and suppleness. In the field of wound treatment, if employed in dry wounds a hydrating action is of importance for improving and adjusting the wound climate and therefore for assisting the healing conditions in the wound. A suitable possibility for combining liquid uptake or absorption with hydration or moistening comprises combining those components which can meet both requirements in one composition. Mixtures of polyacrylates with a high water uptake and retention capacity and hydrocolloids, such as e.g. natural polymers, such as polysaccharides, in particular alginates, hyaluronic acid, carrageens or celluloses, with good hydrating properties are suitable in particular for this.

It is furthermore desirable in cosmetic use in particular, but also in external therapeutic use, to provide a composition which is configured to a certain extent as a leave-on product. For this, the product must be configured such that it can remain on the skin or in the hair practically completely and virtually without residue. Such leave-on products must furthermore have a certain viscosity, to be able to provide the user with a substantial formulation which is easy to apply. Efforts are therefore made to provide compositions which, with little filler or auxiliary substance material, but ideally high active compound contents, nevertheless have a high use viscosity.

Polymers based on polyacrylic acids and salts thereof, in particular so-called superabsorbers or also hydrogels, are suitable in particular for these purposes.

Water-containing hydrogels for wound care are often also on offer as amorphous gels in tubes or syringes. Such gel-like hydrogels are known, for example, from EP 583170, based on pure synthetic polymers, such as e.g. polyacrylate, or based on pure natural structured polymers, such as from WO 97/03710.

Gel-like mixtures of synthetic and natural structured polymers are also disclosed in the prior art, such as e.g. in EP 737703, the subject matter of which is liquid or amorphous polymeric hydrogels from polyester copolymers stabilized with polysaccharides, or from EP 1779836, which discloses hydrodispersions based on mixtures of polyacrylates and hydroxypropyl-guar.

DE 102005035879 discloses an aqueous hydrogel for wound care which, in addition to a synthetic acrylic acid derivative with a high water uptake capacity, contains at least one gel-forming polysaccharide and an electrolyte mixture of at least two different electrolytes. This hydrogel has a water content of at least 50 wt. % and has, according to the disclosure, particularly good absorbing and at the same time hydrating properties with a good modelling capacity and gel dimensional stability.

A disadvantage of such liquid, semi-liquid or gel-like application forms is in principle the high susceptibility to decay and microbial attack, which necessitates preservative measures. In this context, the addition of chemical preservatives in particular is rather undesirable. Physical preservative methods, such as irradiation or heat treatment, have a direct action on the structure of the gel-forming agents and therefore on the viscosity of the composition. These methods often lead to viscosity changes which can be adjusted only with difficulty and are uncontrollable.

Formulations in gel, powder or granule form furthermore as a rule are difficult to apply in and on the wound due to their non-cohesive, unshaped, dimensionally unstable state. Such non-cohesive compositions are also difficult to dose by amount. Furthermore, uniform distribution of the pulverulent/gel-like formulations is a problem.

Those application forms which have a solid, cohesive form and can be matched and adapted well in the configuration of their shape and size to the treatment parts to which they are to be applied are therefore preferably employed. In this context, formulations which are intended for treatments of the skin preferably have a planar configuration which makes simple and uniform application possible. In this context, suitable formulations should moreover have a certain dimensional stability and a mechanical cohesion, so that in addition to first being simple to apply, a further capacity for modelling on or in the treatment area is ideally also possible. It is moreover desirable to provide such planar, dry formulations in a shape and size adapted to the area to be treated, for which a certain mechanical stability of the formulations is likewise necessary.

In order to be able to provide such hydrogels or hydratable, swellable hydrocolloid compositions in a coherent, planar form with the desired properties with respect to preservative treatment, ease of application, dimensional stability and capacity for modelling, these are often offered in a dried form, e.g. in the form of films, sheets, pads or compresses. Dry formulations are also advantageous over water-containing or moist formulations with respect to storage and transportation.

In order to be able to bring hydrocolloids or hydrogel components, in particular polyacrylate gels, into a planar form, e.g. sheet or covering form, a certain mechanical stabilization of the dried hydrogel composition is necessary, since otherwise the material easily disintegrates into granules or powder after drying, e.g. during mechanical reworking, such as cutting into the desired shape, or also already during handling, in particular of dried compositions of large area.

Such dried hydrogel or polymer formulations which, by application to a solid, preferably textile and/or insoluble carrier, are stabilized mechanically and brought into a planar form which can be applied are known from the prior art.

Thus, WO 01/82886 describes a freeze-dried cosmetic "patch" of a rehydratable hydrocolloid composition which can contain natural polysaccharides, such as alginates, semi-synthetic hydrocolloids, such as celluloses, or also synthetic polymers, such as polyacrylates, and which is obtainable by application of the hydrocolloid composition to a solid carrier adhering thereto, e.g. in the form of a nonwoven, a network or a crosslinked foam, e.g. of polyurethane, and subsequent freeze drying. The adhering carrier here is decisive for obtaining an adequate mechanical stability during the freeze drying process and during the later handling and application of the "patches", and makes it first possible to provide the composition in the desired "patch" or mask form. In the processing of polyacrylic acid polymers in the cosmetics industry, the pH is generally neutralized, hence also in the process of the compositions described, which are neutralized by means of sodium hydroxide. This leads to the lack of stability of such compositions in the freeze drying and later handling, which is why application to an insoluble, stabilizing carrier is necessary.

Further dry hydrocolloid or hydrogel compositions in the form of planar sheets or masks which are stabilized by application of the hydrocolloid composition to a solid carrier are known from WO 99/20318 and WO 97/41900, wherein water-soluble hydrocolloid compositions, e.g. based on alginates, are applied to a solid substrate by pouring and are additionally stabilized on this by crosslinking with metal ions, before the formulations are subjected to a freeze drying.

The masks or patches from a mixture of synthetic structured polymers, such as e.g. polyacrylate, and natural hydrocolloids, such as e.g. alginate or cellulose, which are disclosed in DE 60113937 (arising from the abovementioned WO 01/82886), are stabilized by application to a solid fibrous carrier matrix such that the formulations freeze-dried on the carrier can be cut out into the desired shape.

Disadvantages of such formulations fixed to a carrier are the inhomogeneity of the material and, in particular, the need for removal of the insoluble, usually synthetic carrier matrix from or out of the part of the body or also wound to be treated. In particular, when hydrocolloid compositions which can be rehydrated to a gel are used in wound treatment, insoluble or non-rehydratable constituents in the composition are undesirable, since, for example, these are not absorbed or can be flushed out of the wound with the wound exudate only with difficulty. In a cosmetic treatment using a hydrogel composition which can be rehydrated to a viscous gel also, an insoluble carrier matrix is undesirable, since such a carrier layer impedes the incorporation of the active compounds and active substances contained in the composition, in particular e.g. by massage of the hydrated gel composition on the skin. It is also difficult for the hydrogel composition relevant for the treatment to be separated again from the carrier matrix, which as a rule is not relevant for the actual treatment, during use. In this context, on removal of the carrier matrix, a certain amount of hydrogel composition adhering to this or embedded in this is always also removed, which is then no longer available for the actual treatment. As a result, on the one hand a reproducible and accurately dosed application of the treatment agent or of active compounds is not possible, and on the other hand material resources are squandered unused by this means, which is also undesirable from economic aspects.

The provision of mechanically stable, dried hydrocolloid compositions, in particular in a planar configuration, which are stabilized without using such insoluble, planar-cohesive carrier materials is known, for example, from DE 4328329 or WO 01/78692, wherein membranes or masks based on freeze-dried natural structured polymers, for example based on sodium alginates, are disclosed. In this context, the matrices of DE 4328329 are stabilized by the addition of loose spun fibres, such as e.g. textile rayon fibres, or by a calcium crosslinking, such that the cast and freeze-dried blocks can be cut out into the desired mask shape. The freeze-dried gel matrices according to WO 01/78692 are likewise stabilized mechanically by partial crosslinking, in particular by calcium ions. In this context, however, neither document discloses mixtures of natural hydrocolloids with synthetic structured polymers, such as, in particular, those based on polyacrylate and its derivatives.

The documents WO 95/19795 or GB 2401879 also merely disclose dry sheet- or dry sponge-like hydrogel formulations which acquire stabilization by the addition of textile fibres, e.g. of rayon (viscose) or cotton, or of non-swelling synthetic polymer fibres, e.g. based on polyamide, polyester or polyether.

WO 03/051412, in contrast, discloses freeze-dried adsorbent sponge materials, for example in the form of uniform sheets, which are obtainable from synthetic polyacrylic acid polymers and are likewise stabilized with such insoluble, synthetic textile fibre materials, such as, in particular, with carboxymethylcellulose fibres.

The addition of insoluble textile fibres or other non-swelling synthetic fibre constituents to such rehydratable hydrogel formulations, which are soluble by gel formation, for stabilization is undesirable inasmuch as in the rehydrated gel these insoluble textile and non-swelling fibre constituents form an insoluble component which, especially in a cosmetic treatment, requires an expensive and undesirable removal by cleansing after the actual treatment. Such insoluble and non-swellable constituents also are not absorbable or degradable e.g. in a wound, and as particulate foreign bodies in a wound are potential triggers of granulation foci caused by encapsulation processes. Such granulation foci moreover represent a potential risk of infection, which is undesirable in particular in wounds which per se already heal poorly or chronic wounds with generally very unstable wound medium conditions. The particulate foreign bodies must usually be removed from the wound in an involved manner by rinsing.

In the case of stabilization by chemical crosslinking of the composition, the soluble polymer constituents are in principle converted into a water-insoluble composition which is irreversibly firmly bonded under conventional use conditions, as a result of which provision of dry hydrocolloid compositions, in particular in a planar sheet, foam or sponge configuration becomes possible.

Formulations stabilized in this way by crosslinking are also known from, in addition to the DE 4328329, WO 01/78692, WO 99/20318 or WO 97/41900 already cited, for example WO 97/39781 and WO 96/13285, wherein freeze-dried sponges and foams which are stabilized by crosslinking, have a high absorption capacity and are based on natural hydrocolloids are disclosed for wound treatment. Freeze-dried compositions from mixtures of at least one polymer based on polyacrylic acids and salts thereof with at least one natural polymer, such as, in particular, alginates, hyaluronic acid, carrageen or celluloses, which are in the form of a homogeneous, mechanically stable, but in this context carrier- or fibre-free matrix are also not disclosed here.

In contrast, such mixtures are in principle the subject matter of WO 03/068843, wherein so-called interpolyelectrolyte complexes of ionically crosslinked mixtures of polyacrylic acid polymers with chitosans, which belong to the group of natural polymers, are obtained. The gels obtainable via these can also be lyophilized, the configuration in the form of cohesive matrices or coverings not being described. Rather, the dried gels are ground to give a particulate material. An inadequate stability for provision in the form of cohesive sheets can be concluded from this.

Such mixtures are furthermore also known from DE 19710369, which discloses water-insoluble, chemically crosslinked nonwovens or masks for cosmetic use based on chitosan and derivatives, which are crosslinked with crosslinking agents such as, in particular, polyacrylic acids. The adequate stability for provision in the form of masks or nonwovens is achieved here by the chemical crosslinking of the polyacrylate polymer with the natural polymer chitosan, which belongs to the group of cationic polymers, whereas mixtures of polyacrylate/polyacrylate derivatives with so-called anionic natural polymers, such as e.g. alginates, hyaluronic acid, carrageen and/or with celluloses, also are not the subject matter of the disclosure content here.

Stabilizations obtained by crosslinking reactions cannot be rehydrated or can be rehydrated only with great difficulty, with dissociation and gel formation, to thus form soluble compositions. Partial crosslinkings to obtain rehydratable gel compounds, as described in WO 01/78692 or in WO 03/068843, are not suitable for obtaining adequate stabilization to provide mechanically stable, cuttable compositions, especially in the case of hydrogels based on mixtures of polyacrylate/polyacrylate derivatives and natural hydrocolloids. In addition, the dissolving of such a chemical crosslinking requires the addition of specific chemical reagents in the hydration liquid, which on the one hand severely impairs the flexibility in the choice of the composition of such liquids, and moreover is undesirable due to possible potential incompatibilities of such chemical additions.

The object of the present invention was therefore to provide a freeze-dried composition which has a high moisture uptake and retention capacity and in this context nevertheless also has a hydrating, that is to say moistening action and which can be provided in the form of a planar configuration, e.g. in the form of masks, coverings, sheets or pads, and in the form of shaped bodies of large format. This composition should moreover be rehydratable under the addition of hydrophilic liquids to form a homogeneous, finely disperse gel which is substantially free from macroscopic particles or fibre constituents, in order to be suitable in particular for cosmetic and therapeutic skin treatment.

By the combination of natural structure-forming polymers, such as, in particular, those from the group of anionic polymers, in particular from the group of polysaccharides, such as e.g. alginates, with at least one polymer based on polyacrylic acids and salts thereof, such as e.g. in particular those from the group of carbomers, sponge-like compositions or shaped bodies which have an adequate mechanical stability and which can be converted into application forms such as those in the form of masks, sheets, coverings or pads by cutting out can be prepared by freeze drying. Such freeze-dried compositions according to the invention are rehydratable without residue to the greatest extent and rapidly, with gel formation, and have a high moisture uptake and retention capacity and a good hydrating or moistening action.

Freeze-dried compositions which comprise synthetic polyacrylic acid polymers in combination with a natural polymer from the group of alginates are known, for example, from WO 99/65538 and WO 01/28600. In these, wound coverings which, in addition to the abovementioned polymeric hydrocolloids, moreover contain iodine-containing active compounds are described in these. The compositions of WO 99/65538 moreover are preferably prepared at a pH of 3-6.5.

Freeze-dried compositions in the form of a cohesive, sponge-like sheet material containing synthetic polyacrylic acid polymers in combination with a natural polymer from the group of hyaluronic acid and its derivatives are furthermore known, for example, from WO 94/01468, a neutralization with inorganic bases and no working at acid pH values being described herein.

SUMMARY OF THE INVENTION

It has now been found, surprisingly, that such freeze-dried compositions can be improved decisively with respect to their liquid uptake or liquid retention capacity if those synthetic polymers from the group of polyacrylic acids are combined with natural polymers from the group of alginates and with a further natural polymer from the group of hyaluronic acid and its derivatives and optionally from the group of carrageens.

It has furthermore been found, surprisingly, that it was possible for the liquid retention capacity, in particular for physiological fluids, to be improved decisively or kept stable with the compositions according to the invention. This is of particular importance above all in the field of wound treatment, e.g. in wound exudate management, or for the application of physiological active compound solutions, but also in cosmetics in the use of physiological and therefore particularly compatible cosmetic or activator solutions are used.

In this context, the abovementioned desired properties, such as good processability, mechanical stability, in particular high stability on cutting, easy handling and high compatibility etc., are retained. Such an improvement is therefore of great interest in particular for the fields of use mentioned in cosmetic and medical use.

In this context, further natural or synthetic polymers, such as precisely carrageen or, for example, collagen or cellulose or its derivatives, and also active compounds and/or auxiliary substances can moreover be added to such compositions.

None of the documents mentioned discloses a freeze-dried composition in the form of a mechanically stable, cohesive, sponge-like sheet material containing synthetic polyacrylic acid polymers in combination with a natural polymer from the group of alginates and a further natural polymer from the group of hyaluronic acid and its derivatives and optionally from the group of carrageens and/or from the group of collagens and/or celluloses. Furthermore, none of the documents discloses such compositions with an acid pH of from 3 to 6.5 or corresponding compositions which are obtainable by working at such acid pH values.

In the combination of polyacrylates and their derivatives with natural polymers or natural hydrocolloids, such as those from the group of polysaccharides, in particular alginates, carrageenan or celluloses, the very specific interaction between the polymer components in the aqueous mixture is to be taken into account.

The substance class of carbomers (synthetic acrylic acid polymers) comprises bulky branched polymers which carry carboxylic acid groups as essential functional units. These carboxylic acids can have different charge states as a function of the pH.

Aqueous carbomer solutions react acidically, and with an increasing pH or with increasing neutralization and a shift of the pH into the alkaline range the acid groups undergo a deprotonation, as a result of which the polymer matrix becomes negatively charged. Due to the charge shift, an intramolecular repulsion of the negatively charged polymer chain takes place, which results in a three-dimensional unfolding. The carboxylate groups are hydrated and the polymer molecule takes up water and swells. An increase in the intrinsic viscosity results as a measurable effect of the neutralization of the carbomer.

This unfolding of the molecule due to intramolecular electrostatic repulsion and the associated increase in viscosity of an aqueous carbomer solution is highly pH-dependent. This process is reversible, i.e. with increasing protonation the polymer matrix is neutralized, the electrostatic repulsion is reduced and the molecule as it were collapses, as a result of which the viscosity of the solution also decreases.

The reduction in the intrinsic viscosity can also be achieved by the influence of salts or electrolytes such as are contained, for example, in physiological fluids. The viscosity of carbomer-containing solutions is thus a reversible system with a high sensitivity to pH and electrolytes.

A carbomer molecule unfolded by neutralization is capable of undergoing interactions in a composition with other polymers. In particular, electrostatic interactions of differently charged components can lead here to a high interaction potential and therefore to a good mechanical stabilization of subsequently dried matrices. This principle is utilized in particular by so-called "interpolyelectrolyte complexes", as described in "Matrix Polymeric Excipients: Comparing a Novel Interpolyelectrolyte Complex with Hydroxypropylmethylcellulose; Zhilei Lu et al., Drug Delivery, vol. 15, issue 2, 2008, 87-96". In this context, the term "interpolyelectrolyte complexes" is understood as meaning mixtures of differently charged polymers, here in particular a mixture of cationic chitosan (polyaminosaccharide which has free amino groups and can therefore act as a polycation in acidic solution) and anionic carbomer, as also already described in the cited DE 19710369 and WO 03/068843. Due to the electrostatic forces between the oppositely charged polymer components, ionic interactions develop, which are significantly stronger than e.g. van der Weals forces or hydrogen bridge bonds. The polymers are virtually stabilized by "ionic" association or crosslinking.

On the other hand, if mixtures of polymers charged in the same sense, such as, for example, mixtures of an anionic carbomer and an anionic hydrocolloid, such as, for example, alginate or hyaluronic acid or carrageen or collagen, are employed, the stabilizing ionic component is lacking in this composition. In the chosen case of carbomer/alginate, for example, if the neutralization is too high a destabilizing contribution due to the electrostatic repulsion is even obtained. A formulation which is stable in the dry state and contains such hydrocolloid mixtures charged in the same sense can be obtained only if the destabilizing forces between the different polymer components are kept as low as possible, so that the dry composition is effected solely via van der Weals forces or via hydrogen bridge bonds, such interactions having a significantly lower stabilizing action than the electrostatic interactions of oppositely charged polymers.

If carbomers contained in a highly viscous solution and unfolded to the maximum, which have a high negative charge density in the unfolded swollen state, are combined with further anionic hydrocolloids or negatively charged polymers, such as e.g. alginate solutions, the freeze-dried end products of such solutions often have an unsatisfactory mechanical stability because of the electrostatic repulsion of the polymer components charged in the same sense and because of the influence of further constituents of the composition. If the charge density of the anionic polymers in the solution is reduced, e.g. by a shift in the pH, in order to reduce the electrostatic repulsion of the polymers, with the associated protonation of the carboxylate groups the carbomer undergoes a drop in the intrinsic viscosity.

The freeze-dried end products of such compositions of carbomer and hydrocolloids charged in the same sense thus usually have either an inadequate mechanical stability because of an inadequate intrinsic viscosity of the carbomer, or an inadequate mechanical stability because of the electrostatic repulsion of the polymers charged in the same sense. This effect is additionally intensified if such compositions contain further substances having an electrolytic action, to which the carbomers react sensitively as described above.

DESCRIPTION OF THE PREFERRED EMBODIMENTS

For the above reasons, it is therefore preferable to prepare the freeze-dried compositions according to the invention with the pH adjusted to a value of between pH 3.0 and 6.5, preferably between pH 4.0 and 6.0, more preferably between pH 4.5 and 5.5, particularly preferably pH 5.0, in order thereby to obtain particularly mechanically stable, freeze-dried compositions from highly viscous mixtures of a carbomer with a natural hydrocolloid, in particular with an anionic hydrocolloid, such as e.g. an alginate, and with improved liquid uptake and retention properties, in particular with respect to physiological fluids. An undesirable decrease in viscosity or an adverse additional stabilizing of the composition, e.g. by addition of insoluble constituents, such as carrier matrices or fibres or by chemical crosslinking, is said to be avoided by such a pH adjustment.

Those freeze-dried compositions of which a 1 percent strength by weight solution or suspension in water at 20° C. has a pH of from 3.0 to 6.5, preferably between pH 4.0 and 6.0, more preferably between pH 4.5 and 5.5, particularly preferably pH 5.0 are therefore preferred.

It has moreover been found, surprisingly, that those freeze-dried compositions according to the invention with a pH of between pH 3.0 and 6.5, preferably between pH 4.0 and 6.0, more preferably between pH 4.5 and 5.5, particularly preferably pH 5.0 furthermore have an optimum wetting speed, which is of essential importance for the rehydration and conversion into age) for cosmetic use or use as a moisture-absorbing wound covering.

It has furthermore been found, surprisingly, that the freeze-dried compositions according to the invention with a pH of between pH 3.0 and 6.5, preferably between pH 4.0 and 6.0, more preferably between pH 4.5 and 5.5, particularly preferably pH 5.0 have particularly high optical densities. In this context, a direct influence of the pH established on the optical density to be achieved in the freeze-dried compositions is found.

The charge density of the carbomer in this pH range is high enough to ensure a sufficient intramolecular repulsion of the carboxylate groups (high intrinsic viscosity, sufficiently high hydrodynamic radius), without allowing the intermolecular repulsion of the negatively charge carbomers with the further anionic natural polymers or further electrolytically active constituents to become too high. In this pH range the stabilizing of the freeze-dried matrix via hydrogen bridge and van der Waals interactions is sufficiently high for optically dense matrices which are mechanically stable, in particular stable to cutting, to be obtained. If the pH is increased to >pH 6.5, the electrostatic repulsion of the polymer constituents charged in the same sense and the adverse effect on the stabilizing hydrogen bridge bonds and van der Waals forces can become so high that the freeze-dried compositions become mechanically too unstable to form stable shaped bodies of large format or to be able to be converted into the desired shapes by cutting. The wettability of such compositions also deteriorates drastically, as a result of which a pH of the freeze-dried composition of not more than pH 5.5 is particularly preferred.

No freeze-dried compositions with such a polymer composition which can be prepared without additional stabilizing constituents and have corresponding physical, mechanical and chemical properties are known from the prior art.

The invention thus provides freeze-dried compositions which comprise at least one polymer based on polyacrylic acids and salts thereof and at least one natural polymer, and optionally at least one further natural or synthetic polymer which differs from these abovementioned polymers, and optionally one or more active compounds and/or auxiliary substances. The invention furthermore relates to a process for the preparation of such freeze-dried compositions, the combination of such freeze-dried compositions in kit-of-parts arrangements together with aqueous solutions and the use of the freeze-dried compositions and of the kit-of-parts combinations for cosmetic and pharmaceutical use, in particular for use as a cosmetic mask and as a wound covering and for the preparation of pharmaceutical agents for treatment of dermal wounds, such as, in particular, chronic wounds, ulcus cruris or decubitus.

In the context of the invention, freeze-dried composition is also understood as meaning a freeze-dried hydrogel composition, in particular a hydrophilic polymer or a hydrophilic polymer composition, hydrocolloidal, structure-forming polymers in particular forming such a hydrogel composition, and which are capable of swelling in aqueous liquids, with an increase in volume and increase in viscosity. As a result, such compositions in the context of the present invention have a high liquid uptake and storage capacity, or a high water content in the swollen, hydrated state.

The freeze-dried compositions of the present invention comprise at least one polymer based on polyacrylic acids and salts thereof, specifically polyacrylic acid, such as polyacrylates and their derivatives, such as those having the basic structure

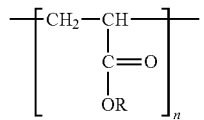

where R=—H (polyacrylic acid), or R=alkyl group (polyacrylates). These can be amorphous and branched, and substituted by further functional groups or also present in various forms by derivatization of the basic matrix. In this context, selective chemical changes relate in particular to the carboxylic acid groups, e.g. by esterification. The formation of mixed copolymers (e.g. block copolymers) from the polyacrylic acid basic matrices is also possible.

The acrylic acid polymers which are particularly preferred according to the invention are, for example, acrylate/alkyl acrylate copolymers, in particular those based on synthetic acrylic acid polymers, which are also known by the generic name "carbomers" and according to the USP-NF, British Pharmacopoeia, United States Adopted Names Council (USAN) and Cosmetic Toiletries and Fragrance Association (CTFA) include the group of Carbopols (Carbopol®, B. F. Goodrich Company).

Chemically, such carbomers are acrylic acid polymers, more precisely a copolymer of acrylic acid and sodium acrylate, wherein the ratio of the monomers with respect to one another can vary. Homopolymers of acrylic acid which are crosslinked with pentaerythritol allyl ether, sucrose allyl ether or propylene allyl ether, such as, for example, copolymers of $C_{10}$-$C_{30}$-alkyl acrylates and one or more monomers of acrylic acid, methacrylic acid or esters thereof, which are cross-crosslinked with an allyl ether of sucrose or an allyl ether of pentaerythritol, also fall under the group of carbomers.

Because of the particularly good water uptake capacity of the acrylic acid polymers, such as, in particular, the carbomers, these are also known by the term "superabsorbers", which conventionally describes those polymers which are capable of taking up several times their own weight—up to 1,000 times—of liquids (usually water or distilled water). In this context, the actual uptake capacity depends in particular on the composition of the aqueous liquids. If the liquid is, for example, pure water, the absorption capacity for this is as a rule significantly higher than, for example, for salt- or electrolyte-containing liquids, such as e.g. physiological saline solutions or physiological body fluids. This is possibly to be attributed to the sensitivity of this substance group to electrolytes which has already been discussed. If the molecular structure is influenced due to electrolytes such that the intrinsic viscosity decreases, the molecule thus reduces its spatial extent, a lower capacity for embedding water molecules into the gel or polymer structure results, as a result of which the water absorption capacity is in general lowered.

Reference is made to the above statements with regard to the structure and action and the associated particular properties with respect to the physical nature of solutions and the pH and electrolyte-sensitivity of such carbomer molecules.

The freeze-dried compositions according to the invention furthermore comprise at least one natural polymer. In this context, one from the group of natural structure-forming polymers is preferably chosen, preferably from the group of polysaccharides or glycosaminoglycans. In this context, it has been found, surprisingly, that with the composition and preparation method present according to the invention it is possible in particular to combine anionic hydrocolloid-forming natural polymers with the polyacrylic acids. The natural polymers are preferably chosen from the polysaccharides. Polysaccharides include, for example, homoglycans or heteroglycans, such as, for example, alginates, in particular sodium alginate, carrageen (where appropriate also mentioned herein under the equivalent English name "carrageenan"), pectins, pullulan, tragacanth, guar gum, carob bean flour, agar-agar, gum arabic, xanthan, natural and modified starches, dextrans, dextrin, maltodextrins, chitosan, glucans, such as β-1,3-glucan and β-1,4-glucan, such as cellulose, mucopolysaccharides, such as hyaluronic acid etc. In this context, anionic hydrocolloid-forming natural polymers describe those naturally occurring polymers which form viscous solutions in aqueous solution. They are polyelectrolytes and have ionizable functional groups which carry a negative charge in the biological (neutral) pH range.

Such anionic natural hydrocolloids are, for example, alginates, hyaluronic acid, carrageen, carboxymethylcellulose, gum arabic, agar-agar, collagen, gelatine type B, karaya gum, pectin, tragacanth, poly-methyl vinyl ether/maleic anhydride (Gantrez) etc.

The natural polymers preferably employed according to the invention, such as, in particular, those from the group of polysaccharides, expediently have average molecular weights of from about $10^3$ up to about $10^8$, preferably about $10^4$ to $10^8$.

From the group of natural polymers, those from the group of alginates, such as, in particular, sodium alginate, are particularly preferred according to the invention. Calcium-free sodium alginates (sodium alginate with a calcium content of <3 wt. %, more preferably <2 wt. %, still more preferably <1.5 wt. %) are preferred.

The composition can furthermore also comprise one or more further polymers from the group of natural polymers, such as e.g. those as mentioned above, or also those such as, for example, collagens or derivatives thereof, such as e.g. soluble or insoluble animal or plant collagen, in particular e.g. fish collagen. However, it is also possible to choose a further polymer which differs from those mentioned above, e.g. those from the group of further synthetic and/or modified natural polymers. Such synthetic or modified natural polymers include, for example: cellulose ethers, polyvinyl alcohol, polyvinylpyrrolidone, synthetic cellulose derivatives, such as methylcellulose, carboxycellulose, carboxymethylcellulose, cellulose esters, cellulose ethers, such as hydroxypropylcellulose, polyacrylic acid, polymethacrylic acid, poly(methyl methacrylate) (PMMA), polymethacrylate (PMA), polyethylene glycols etc.

It is preferable for at least one further natural polymer to be chosen from the group of carrageens, such as, in particular, carrageenan, and/or from the group of mucopolysaccharides, such as, in particular, hyaluronic acid, and/or from the group of collagens, such as, in particular, fish collagen, It is furthermore preferable for at least one further polymer to be chosen from the group of synthetic and/or modified natural polymers from the group of modified celluloses, in particular from these carboxymethylcelluloses is preferred, in particular sodium carboxymethylcellulose.

It is also possible to use mixtures of several polymers from the group of natural polymers and/or from the group of synthetic polymers. Mixtures of alginates and hyaluronic acid and optionally carrageen and/or collagen and/or celluloses are particularly preferred.

The polymers of the freeze-dried composition according to the invention have a good biocompatibility and in particular are tolerated by skin and mucous membranes and have no toxicological potential when used on intact skin nor when introduced into one of the lower layers of skin, e.g. in wounds in which the natural skin structure is injured or destroyed. The polymers according to the invention also cause no irritation actions or other intolerance reactions at all when applied. They are completely pharmacologically acceptable and therefore suitable in an optimum manner as polymer material for the cosmetic and pharmaceutical dermal uses according to the invention.

The compositions according to the invention can moreover also comprise at least one or more active compounds. Such freeze-dried compositions according to the invention preferably comprise at least one active compound. Active compounds include, in particular, cosmetic or therapeutic or pharmaceutical active compounds which are suitable for external use. Such freeze-dried compositions according to the invention are accordingly preferably cosmetic or therapeutic agents.

In the context of the invention, cosmetic agents or agents prepared using cosmetic active composition are essentially agents in the sense of the Foodstuffs, Commodities and Feedstuffs Code [German LFGB], i.e. substances or formulations of substances which are intended for use externally on humans for cleansing, care, or for influencing the appearance or the body odour, or for imparting odoriferous impressions, unless they are predominantly intended for alleviation or elimination of diseases, suffering, body damage or pathological symptoms. In this context, the cosmetic shaped bodies used according to the invention are, for example, bath preparations, skin washing and cleansing agents, skin care agents, in particular facial skin care agents, eye cosmetics, lip care agents, nail care agents, foot care agents, hair care agents, in particular hair shampoos, hair conditioners, hair softeners etc., light protection agents, skin tanning and lightening agents, depigmentation agents, deodorants, antihydrotics, hair removal agents, insect repellents etc., or such agents in combination.

Examples of cosmetically, optionally also e.g. dermatological, therapeutically active compounds include: antiacne agents, antimicrobial agents, antiperspirant agents, astringent agents, deodorizing agents, hair removal agents, conditioning agents for the skin, skin-smoothing agents, agents for increasing skin hydration, such as e.g. glycerol or urea, sunscreen agents, keratolytics, free radical scavengers for free radicals, antiseborrhoea agents, antidandruff agents, antiseptic active compounds, active compounds for treatment of signs of ageing of the skin and/or agents which modulate the differentiation and/or proliferation and/or pigmentation of the skin, vitamins, such as vitamin C (ascorbic acid) and its derivatives, such as, for example, glycosides, such as ascorbyl glucoside, or esters of ascorbic acid, such as sodium or magnesium ascorbyl phosphate or ascorbyl palmitate and stearate, L-ascorbic acid phosphate esters, alkali metal salts, such as sodium and potassium salts, of L-ascorbic acid phosphate esters; alkaline earth metal salts, such as magnesium and calcium salts, of L-ascorbic acid phosphate esters; trivalent metal salts, such as aluminium salts, of L-ascorbic acid phosphate esters; alkali metal salts of L-ascorbic acid sulfate esters, such as sodium and potassium salts of L-ascorbic acid sulfate esters; alkaline earth metal salts, such as magnesium and calcium salts, of L-ascorbic acid sulfate esters; trivalent metal salts, such as aluminium salts, of L-ascorbic acid sulfate esters; alkali metal salts, such as sodium and potassium salts, of L-ascorbic acid esters; alkaline earth metal salts, such as magnesium and calcium salts, of L-ascorbic acid esters; and trivalent metal salts, such as aluminium salts, of L-ascorbic acid esters.

Active compounds having an irritant side effect, such as alpha-hydroxy acids, β-hydroxy acids, alpha-keto acids, β-keto acids, retinoids (retinol, retinal, retic acid), anthralins (dioxyanthranol), anthranoids, peroxides (in particular benzoyl peroxide), minoxidil, lithium salts, antimetabolites, vitamin D and its derivatives; catechols, flavonoids, ceramides, polyunsaturated fatty acids, essential fatty acids (e.g. gamma-linolenic acid), enzymes, coenzymes, enzyme inhibitors, hydrating agents, skin soothing agents, detergents or foam-forming agents, and inorganic or synthetic matting fillers, or decorative substances, such as pigments or dyestuffs and coloured particles for foundations, make-up formulations, and other agents for cosmetic adornment and coloured modelling of eyes, lips, face etc. and abrasive agents.

Plant active compound extracts or extracts or individual substances obtained therefrom may furthermore be mentioned. Generally, the plant active compound extract is as a rule chosen from the group consisting of solid plant extracts, liquid plant extracts, hydrophilic plant extracts, lipophilic plant extracts, individual plant constituents; and mixtures thereof, such as flavonoids and their aglyca: rutin, quercetin, diosmin, hyperoside, (neo)hesperidin, hesperitin, *Ginkgo biloba* (e.g. ginkgoflavone glycosides), *Crataegus* extract (e.g. oligomeric procyanidins), buckwheat (e.g. rutin), Sophora japonica (e.g. rutin), birch leaves (e.g. quercetin glycosides, hyperoside and rutin), elder blossom (e.g. rutin), linden blossom (e.g. essential oil with quercetin and farnesol), St. John's wort oil (e.g. olive oil extract), *Calendula*, Arnica (e.g. oily extracts of the blossom with essential oil, polar extracts with flavonoids), Melissa (e.g. flavones, essential oil); immunostimulants: Echinacea purpurea (e.g. alcoholic extracts, fresh sap, pressed juice), Eleutherococcus senticosus; alkaloids: Rauwolfia (e.g. prajmalin), periwinkle (e.g. vincamin); further phytopharmaceuticals: Aloe, horse chestnut (e.g. aescin), garlic (e.g. garlic oil), pineapple (e.g. bromelains), ginseng (e.g. ginsenosides), Our Lady's thistle fruit (e.g. extract standardized with regard to silymarin), box holly root (e.g. ruscogenin), valerian (e.g. valepotriates, tct. Valerianae), kava kava (e.g. kava lactones), hop blossom (e.g. hop bitters), etr. Passiflorae, gentian (e.g. ethanol. extract), anthraquinone-containing drug extracts, e.g. aloin-containing Aloe vera juice, pollen extract, algae extracts, liquorice extracts, palm extract, Galphimia (e.g. original tincture) mistletoe (e.g. aqueous ethanol. extract), phytosterols (e.g. beta-sitosterol), verbascum (e.g. aqueous alcohol. extract), Drosera (e.g. vinum liquorosum extract), sea buckthorn fruit (e.g. juice obtained therefrom or sea buckthorn oil), marshmallow root, primula root extract, fresh plant extracts of mallow, comfrey, ivy, horsetail, yarrow, ribwort (e.g. pressed juice), stinging nettle, greater celandlne, parsley; plant extracts from Norolaena lobate, Tagetes lucida, Teeoma siems, Momordica charantia, and Aloe vera extracts.

Preferred cosmetic active compounds are those which have a high instability towards degradation or decomposition, in particular caused by supplying moisture, and which, by using the freeze drying process, can be provided in these formulations in a form stabilized towards moisture.

A particularly preferred active compound from the group of these unstable active compounds which is widely used in particular in cosmetics is ascorbic acid (vitamin C) and its derivatives, such as, for example, ascorbyl glucoside. L-ascorbic acid phosphate esters, alkali metal salts, such as sodium and potassium salts, of L-ascorbic acid phosphate esters; alkaline earth metal salts, such as magnesium and calcium salts, of L-ascorbic acid phosphate esters; trivalent metal salts, such as aluminium salts, of L-ascorbic acid phosphate esters; alkali metal salts of L-ascorbic acid sulfate esters, such as sodium and potassium salts of L-ascorbic acid sulfate esters; alkaline earth metal salts, such as magnesium and calcium salts, of L-ascorbic acid sulfate esters; trivalent metal salts, such as aluminium salts, of L-ascorbic acid sulfate esters; alkali metal salts, such as sodium and potassium salts, of L-ascorbic acid esters; alkaline earth metal salts, such as magnesium and calcium salts, of L-ascorbic acid esters; and trivalent metal salts, such as aluminium salts, of L-ascorbic acid esters.

In contrast to the compositions described above which are essentially used in the cosmetics field, the therapeutic compositions (medicaments) are those which comprise at least one pharmaceutical or therapeutic, in particular also dermatological active compound and which in the sense of medicaments legislation are intended, inter alia, for curing, for alleviating or for preventing diseases, suffering, bodily damage or pathological symptoms. In particular, those agents or active compounds which are intended for external or transdermal use, in particular in the field of wound treatment and healing, are suitable according to the invention.

Active compounds for such a dermal or transdermal use are, in particular, active compounds which are active on the skin, but also transdermal active compounds. They include, for example: agents for treatment of skin diseases, analgesics which can be used externally, e.g. dextropropoxyphen, pentazocine, pethidine, buprenorphine; antirheumatics/antiphlogistics (NSAR), e.g. indometacin, diclofenac, naproxen, ketoprofen, ibuprofen, flurbiprofen, salicylic acid and derivatives, such as acetylsalicylic acid, oxicams; steroid hormones, e.g. betamethasone, dexamethasone, methylprednisolone, ethynyloestradiol, medroergotamine, dihydroergotoxin; gout agents, benzbromarone, allopurinol; external dermatics, antihistamines, antibiotics, including antibacterial agents, such as e.g. colloidal silver and silver salts, antimycotics, peptide medicaments, antiviral active compounds, antiinflammatory active compounds, antipruritic active compounds, anaesthetizing active compounds, e.g. benzocaine, corticoids, acne agents, antiparasitic active compounds; hormones which can be used externally; vein therapeutics; immunosuppressants etc., all for dermal or transdermal use.

Preferred therapeutic agents for dermal and transdermal use are agents for treatment of skin diseases, such as neurodermatitis, atopic dermatitis etc., and anti-herpes agents, and, in particular, those which are employed in the field of wound treatment, in particular for treatment of chronic wounds, decubitus, ulcus cruris etc., such as, for example, analgesics, e.g. immunosuppressants, hormones, anaesthetizing active compounds, antiparasitic, fungicidal or antimycotic and antibacterial active compounds, such as, in particular, silver-containing active compounds, such as e.g. silver nitrate, silver chloride, silver iodide or further silver-containing wound treatment substances known from the prior art, active compounds for assisting and regulating the wound medium, such as, in particular, electrolytes, silica, mineral substances and trace elements, such as e.g. potassium, magnesium, calcium, selenium, iodine etc., and active compounds for achieving wound debridement, such as e.g. collagenases or other suitable proteolytic enzymes known in the prior art.

It is furthermore conceivable to administer further active compounds, such as bronchial therapeutics, such as antiasthmatics, antitussives, mucolytics etc., antidiabetics, such as e.g. glibenclamide, hormones, steroid hormones, such as dexamethasone, cardiac glycosides, such as digitoxin, cardiovascular therapeutics, such as e.g. beta-blockers, antiarrhythmics, antihypertensives, calcium antagonists etc., psychopharmaceuticals and antidepressants, such as e.g. tricyclic antidepressants (NSMRI), serotonin reuptake inhibitors (SSRI), noradrenaline reuptake inhibitors (NRI), serotonin-noradrenaline reuptake inhibitors (SNRI), monoaminooxidase inhibitors (MAO inhibitors) etc., neuroleptics, anticonvulsives or antiepileptics, hypnotics, sedatives, anaesthetics, gastrointestinal therapeutics, lipid-lowering agents, analgesics, such as e.g. antimigraine agents, paracetamol, salicylic acid and derivatives, such as acetylsalicylic acid, diciophenac, ibuprofen, ketoprofen, naproxen etc., antiphlogistics, vasodilators, diuretics, gout agents, cytostatics, muscle relaxants, contraceptives, e.g. in the form of hormone patches, addiction withdrawal agents in the form of, for example, nicotine patches, plant extracts, provitamins, such as e.g. beta-carotene, vitamins, such as e.g.

vitamin C, A, B, E etc., via a transdermal application in a composition according to the invention, e.g. in the form of a transdermal active compound patch.

Particularly preferred pharmaceutical active compounds are those which are chosen from the group of antibacterial agents, such as, in particular, silver compounds or other bacteriostatic/bacteriocidal substances, such as, for example, octinidin, PVP-iodine etc., for treatment of chronic wounds or so-called problem wounds.

The hydrocolloids, in particular those based on natural polymers, such as polysaccharides, can also have certain therapeutic actions. Thus, the hydrocolloid preferably used, (sodium) alginate, to a certain extent has an antiviral action, and hyaluronic acid is said to have a certain action in skin care in re-epithelialization and as an antioxidant and moisture donor, but they are not active compounds in the context of the invention.

The freeze-dried compositions according to the invention can furthermore optionally comprise one or more auxiliary substances. Auxiliary substances include: pH-adjusting agents, such as buffer substances, inorganic and organic acids or bases; fat substances, such as mineral oils, such as paraffin oils or Vaseline oils, silicone oils, plant oils, such as coconut oil, sweet almond oil, apricot oil, maize oil, jojoba oil, olive oil, avocado oil, sesame oil, palm oil, eucalyptus oil, rosemary oil, lavender oil, pine oil, thyme oil, mint oil, cardamom oil, orange blossom oil, soya oil, bran oil, rice oil, rapeseed oil and castor oil, wheat germ oil and vitamin E isolated therefrom, evening primrose oil, plant lecithins (e.g. soya lecithin), sphingolipids/ceramides isolated from plants, animal oils or fats, such as tallow, lanolin, clarified butter, neutral oil, squalane, fatty acid esters, esters of fatty alcohols, such as triglycerides, and waxes having a melting point corresponding to skin temperature (animal waxes, such as beeswax, carnauba wax and candelilla wax, mineral waxes, such as microcrystalline waxes, and synthetic waxes, such as polyethylene or silicone waxes), and all oils suitable for cosmetic purposes (so-called cosmetic oils), such as are mentioned, for example, in the CTFA publication Cosmetic Ingredient Handbook, 1st ed., 1988, The Cosmetic, Toiletry and Fragrance Association, Inc., Washington, surface-active agents in addition to the abovementioned washing surfactants, such as dispersing agents, wetting agents, emulsifiers etc.; fillers, stabilizers, cosolvents, pharmaceutically and cosmetically common or other dyestuffs and pigments, in particular those which are primarily employed for colouring the hydrogel composition and not for application to and colouring on the human body, such as those pigments and dyestuffs such as the decorative dyestuffs listed under the group of active compounds; preservatives; softeners; lubricants or slip agents; etc.

A particularly preferred auxiliary substance is potassium hydroxide solution (KOH) for adjusting the preferred pH of between pH 3.0 and 6.5, preferably between pH 4.0 and 6.0, more preferably between pH 4.5 and 5.5, particularly preferably pH 5.0.

Further auxiliary substances which are preferred according to the invention are fats and oils. In this context, cosmetic oils as listed above, in particular triglycerides, particularly preferably caprylic/caproic acid triglycerides, squalane and/or jojoba oil, are preferred in particular.

A further preferred auxiliary substance is chosen from the group of fillers, mannitol being particularly preferably contained in the composition.

Generally, the classification of the abovementioned substances into the category of auxiliary substances in the context of the present invention does not rule out the fact that these auxiliary substances may also display certain cosmetic and/or therapeutic actions, which applies to a particular degree to the cosmetic oils mentioned which are preferably employed.

Auxiliary substances can be added to the compositions according to the invention in amounts of up to 50 wt. %, based on the freeze-dried total composition of the end product.

The invention moreover provides a process for the preparation of freeze-dried compositions, which comprises the following steps:
a) preparation of an aqueous suspension or a solution of at least one natural polymer
b) optionally mixing in of at least one further polymer which differs from the polymer used in step a) or e)
c) optionally mixing in of one or more active compounds and/or auxiliary substances.
d) adjustment of the pH of the aqueous suspension or solution to a pH of from pH 3.0 to pH 6.5
e) preparation of an aqueous suspension or a solution of a polymer based on polyacrylic acids and salts thereof and adjustment of the pH of the solution to a pH of between pH 3.0 and pH 6.5 with alkalis
f) combining of the suspensions or solutions prepared under a)-d) and under e) and if appropriate adjustment of the pH to pH 3.0 to 6.5
g) pouring or spreading out of the mixture into a suitable mould or on to a suitable surface
h) freezing of the mixture and
i) freeze drying of the mixture to form the freeze-dried composition.

Further steps can optionally be carried out between these steps, and in particular it is possible, after step h), to remove the frozen compositions from the mould optionally used.

After the preparation process described above, the freeze-dried compositions can be converted into the desired shape, in particular by cutting and stamping. In particular, it is possible to provide virtually any desired shape by cutting out the freeze-dried compositions obtainable by the process mentioned. In particular, both the thickness of the compositions and the geometric shape can be adapted by the cutting out.

To obtain compositions in the form of planar configurations, such as e.g. sheets, matrices, coverings, pads, nonwovens, masks, leaves, layers, coatings or in other conceivable planar forms, the freeze-dried compositions which are obtainable by the process described above are preferably cut out to a thickness of from 0.5 mm to 2 cm.

Cut-out pieces in which the length and width of the freeze-dried composition are at least 10 times, preferably at least 20 times the thickness are furthermore preferably chosen.

It is also possible to provide cut-out pieces which are adapted in their geometric shape e.g. to the area of the body to be treated, or those which have imagined shapes. Thus, for cosmetic use in particular, the freeze-dried compositions according to the invention can thus have cut-out pieces in the form of a face or other parts of the body to be treated. In such a case, the compositions according to the invention are in the form of masks.

However, it is also possible to obtain freeze-dried compositions in the form of mechanically stable shaped bodies of large format by the process described above, the configuration of such shaped bodies being determined decisively by the choice of the mould in which the compositions are frozen.

For therapeutic use it is advantageous in particular to cut out sheets or pads in the form of rectangular pieces. Such rectangles can have areas of preferably at least about 25 cm$^2$, more preferably of at least about 50 cm$^2$, still more preferably of at least about 100 cm$^2$, depending on the size of the area to be treated.

In this context, the size, the area and the thickness of the freeze-dried composition is determined, inter alia, by the desired form of application or the site of use. Thus, in the case of external cosmetic or pharmaceutical use, application to relatively large areas of the body or the hair (e.g. direct application of the rehydrated composition to the back etc., or the use as a bath additive) makes possible the use of larger configurations of the compositions, whereas in the case of use on smaller parts of the body (e.g. cheek etc.), smaller configurations of the compositions are preferred. For therapeutic treatment also, adaptation of the size of the composition e.g. to the spatial extent of a wound is of importance.

The hydrogel compositions obtainable by the process described can moreover be stamped or provided with embossing.

Planar configurations of the freeze-dried composition according to the invention preferably have an area of from 5 to 500 cm$^2$, this area resulting from the two longest side lengths of such planar compositions.

During the preparation, a procedure is expediently followed in which an aqueous solution of the natural polymer is first prepared and the further polymers optionally to be added, from the group of natural, modified natural or synthetic polymers, are then added. These can either be mixed directly into the aqueous polymer solution and dissolved therein, or aqueous solutions or suspensions of these further polymers are prepared and are then mixed with the solution or suspension of the natural polymer. Optionally the active compound or compounds and optionally one or more auxiliary substances are added and mixed into this polymer solution or suspension obtainable in this way. After thorough mixing of all the constituents, the pH of the composition is adjusted, if appropriate, to a pH of between pH 3.0 and 6.5, preferably between pH 4.0 and 6.0, more preferably between pH 4.5 and 5.5, particularly preferably pH 5.0, by addition of an auxiliary substance from the group of pH-adjusting agents, preferably with an inorganic alkali, such as, preferably a potassium hydroxide solution.

At least one polymer based on polyacrylic acids and salts thereof, preferably a carbomer, is then added to the mixture. This is carried out by preparation of a polyacrylic acid or carbomer solution partly neutralized with a pH-adjusting agent, such as, in particular, an alkali metal hydroxide solution, such as preferably with potassium hydroxide, which is then incorporated by stirring into the already prepared solution of the natural polymer and the further substances optionally added.

If oil-soluble active compounds are used for the preparation of the solution or suspension which is subjected to the freeze drying, these are preferably dissolved in oils optionally used as auxiliary substances (in particular squalane, jojoba oil and/or triglycerides, such as neutral oil), and the solution of the natural polymer and optionally further polymers and active compounds and/or auxiliary substances are than added. This mode of preparation has the advantage that solutions or suspensions which are stable in the short term are formed. No emulsifiers or surface-active substances, such as e.g. surfactants, are required, and no phase separation of the solution or suspension, if oil-soluble or oily auxiliary substances or active compounds are used, takes place during processing. Preferably, however, water-soluble active compounds are used.

So that the freeze-dried compositions have an adequate mechanical stability, in particular for the cutting out and/or stamping, after the freeze drying, it is necessary for the aqueous solution or suspension of the polymer composition according to the invention to have a certain polymer concentration, in particular of the polymer from the group of natural polymers and polyacrylic acid or derivatives. The particular precise concentration depends of course on the nature of the polymers used. It is expediently about at least 0.5 wt. %, based on the total amount of the solution or suspension subjected to the freeze drying, preferably at least about 1.0 wt. % up to at least about 1.5 wt. %, preferably less than 10 wt. %, still more preferably less than 5 wt. % (weight of the polymers from the group of natural and optionally modified natural and/or further synthetic polymers plus weight of the polyacrylic acids, based on the total weight of the solution.

The solution or suspension prepared in this way is then poured either into suitable moulds or on to a surface and frozen. The cooling or freezing of the solution or suspension can be carried out parse in any desired manner, such as, for example, by blowing cold air on to it, cooling by application to a plate through which cooling brine flows, or also immersion of the moulds in liquid gases, such as e.g. immersion in liquid nitrogen. In this context, the speed of cooling influences the size of the ice crystals formed. These in turn influence the pore size distribution of the frozen hydrogel formed. If few large crystals are formed, the frozen composition has few large pores, and if many small crystals are formed, it has many small pores. The crystals become smaller the higher the speed of cooling of the solution or suspension. In this context, a freezing geometry in which the composition is frozen at a temperature of at least <−20° C. on a cold plate is preferred.

The freezing temperature required depends inter alia on how great the lowering of the freezing point by the active compounds or auxiliary substances contained in the solution is. The temperature expediently lies below the freezing point of water down to the temperature of liquid nitrogen (−196° C.). The freezing temperature is preferably about −10 to −80° C., particularly preferably −20 to −60° C.

The frozen compositions are then subjected to the freeze drying. The freeze drying can be carried out in a manner known per se by generally known freeze drying processes, such as also described e.g. in DE 4328329 C2, DE 4028622 C2 or DE 10350654 A1.

The amount of solids contained in the solution or suspension to be freeze-dried, such as natural, modified natural or synthetic polymers, active compounds and auxiliary substances, decisively influences the density (weight of the freeze-dried composition based on the volume of the geometric form thereof) of the freeze-dried composition obtained. The density in turn is an important parameter for the porosity of the freeze-dried composition and therefore in turn for the speed of dissolving or swellability thereof when moistened with water, an active compound and/or auxiliary substance solution and/or with body or wound fluids. The porous structure of freeze-dried compositions is an essential basis for the rapid uptake of liquid and good rehydration, since due to the large surface area in the porous material, intimate exchange can take place between the aqueous phase and solid composition during the rehydration process. The higher the concentration of polymers and optionally active compounds and auxiliary substances in the solution, the higher the density and therefore the lower the degree of porosity of the freeze-dried composition and vice versa. Nevertheless, the degree of porosity of the freeze-dried compositions does not depend solely on the density of the material. Rather, the porosity of the material is essentially a function of two parameters, the density of the material and the size of the ice crystals. High solids contents in the aqueous suspension increase the density of the material in the freeze-dried end product and reduce the rehydrating agent/solid contact area. High freezing gradients lead to small ice crystals, which lead to large internal material surface areas, which in turn promotes rehydration. Low densities of the material and small ice crystals are thus advantageous for rapid moistening and dissolving or swelling of the freeze-dried compositions.

Under the aspect of density/degree of porosity or speed of dissolving or rehydration, the recipe creation and preparation of the compositions according to the invention is directed such that the densities of the compositions thereby obtainable are expediently about 0.01 g/cm³ up to 0.8 g/cm³, preferably about 0.015 g/cm³ up to 0.5 g/cm³, preferably about 0.02 g/cm³ to 0.1 g/cm³. The term density as used in the present case means the weight of the freeze-dried composition based on the volume of the external geometric form thereof. In this context, the weight of the individual cut-out freeze-dried compositions depends of course on the size thereof and, per dosage unit, that is to say per cut-out piece for the use envisaged at the end, is in general about 10 mg to 6 g, preferably 20 mg to 1,000 mg, still more preferably 50 mg to 500 mg at areas of about 5 to 500 cm², preferably at least 10 cm², more preferably of at least about 15 cm², still more preferably of at least about 20 cm² and thicknesses of from about 0.5 mm to 2 cm.

In particular for aesthetic reasons also, especially in cosmetic, but also in therapeutic use, those compositions which moreover have a high optical density are desirable. In this context, optical density means the quantitative unit of optical density measured as the logarithm to the base ten of the quotient of the intensity of the transmitted light to the intensity of the incident light, determined with a Heiland SW densitometer TD 03 on freeze-dried compositions having a layer thickness of 1 mm. The freeze-dried compositions of the present invention preferably have an optical density of ≥0.02, more preferably ≥0.03, still more preferably ≥0.05 per mm layer thickness.

On the basis of the influence described above for the pH of the compositions according to the invention on the optical density to be achieved, the preparation and recipe creation, in particular the adjustment of the pH, are carried out such that the highest possible optical densities, preferably optical densities of ≥0.02, more preferably ≥0.03, still more preferably ≥0.05 per mm layer thickness are achieved.

The freeze-dried compositions according to the invention can be rehydrated rapidly and virtually completely when liquid is supplied, to form a homogeneous, finely disperse gel, hydrophilic or aqueous liquids being suitable in particular for a rapid rehydration. The polymers employed according to the invention are not soluble in the actual sense, to the extent that the solid constituents are dissolved completely in a solvent and homogeneously distributed therein, but rather swelling and rehydration of the polymers takes place with large amounts of water and ions being embedded in the polymer matrix of the hydrocolloids.

After the rehydration and in the swollen state, in this context the rehydrated composition according to the invention, specifically in view of the desired rapid and residue-free or uniform and homogeneous dissolving or rehydration properties and the good compatibility, is free from visible, macroscopic particles or fibre constituents, such as e.g. textile rayon (viscose) or cotton fibres, or from non-swelling synthetic polymer fibres, e.g. based on polyamide, polyester or polyether. In this context, the gels formed in particular are free from such visible, macroscopic constituents having a size of >5 mm. Freeze-dried compositions which contain no textile fibre constituents are thus preferred according to the invention.

The freeze-dried compositions according to the invention furthermore are not chemically crosslinked and are therefore free from chemical crosslinking agents.

The freeze-dried compositions according to the invention preferably have a viscosity of from 10 to 200 mPas on rehydration of 3 g of the composition in 97 g of distilled water at a temperature of 20-25° C. and a pH value of pH from 4.0 to 6.0. In this context, the viscosity is measured with a Viskotester VT 2 plus with spindle no. 1 from Haake.

The freeze-dried compositions according to the invention are distinguished by their particular speed of wetting and their particular absorption and liquid uptake and storage capacity. In particular, the freeze-dried compositions according to the invention are distinguished by their particular uptake and storage capacity for physiological fluids.

In this context, the liquid uptake or storage capacity of the freeze-dried compositions according to the invention means the ability to take up amounts of liquid, in particular in combination with the ability to store and to hold these amounts of liquid taken up. In this context, those freeze-dried compositions which are capable of taking up and storing amounts of liquid of 1 to 200 times, preferably 10 to 100 times their own weight are preferred according to the invention.

$$Q_M = \frac{m_{gel}}{m_{dr.sa.}}$$

In this equation, the mass degree of swelling ($Q_M$) denotes the amount of liquid which can be taken up by the composition according to the invention. $Q_M$ in this context denotes the ratio of the weight of the swollen composition ($m_{gel}$) to the weight of the dry composition before the swelling ($m_{dr.sa}$).

To measure the mass degree of swelling, the freeze-dried composition is therefore weighed and then laid on the surface of the water in a dish with an excess of distilled water with a temperature of 15-25° C. and left to swell for 10 minutes. The excess water is poured off without mechanical action. After renewed measurement of the weight of the swollen composition, the mass degree of swelling is determined in accordance with the above formula.

The freeze-dried compositions according to the invention preferably have a mass degree of swelling of 15-100.

It is moreover possible to state the liquid retention capacity based on the weight of the composition. For this, after the excess liquid has been poured off the weight increase of the swollen material samples is determined in the experimental set-up described above, converted to the volume of liquid corresponding to this weight increase and this volume of liquid taken up is stated, based on 1 g of the composition employed.

In one aspect of the invention, a plurality of the freeze-dried compositions or cut-out pieces mentioned is contained in one container. These can also be mixtures of cut-out pieces of different geometries or different sizes, e.g. for parallel treatments of various parts of the body. The cut-out pieces can be packed individually, which is preferred in particular in the therapeutic or pharmaceutical use. Cut-out pieces for cosmetic use preferably lie in a plurality side by side or one above the other in contact in a suitable container or a suitable packaging.

The freeze-dried compositions according to the invention serve for external cosmetic and external and transdermal pharmaceutical use in humans and animals. In this context, external use in cosmetic application in particular is carried out such that the composition according to the invention is moistened with water or an aqueous solution containing one or more active compounds and/or one or more auxiliary substances and is dissolved or rehydrated to form a homogeneous gel, this gel being free from visible, macroscopic particles or fibre constituents, such as, in particular, stabilizing textile or non-swellable fibre constituents.

If the freeze-dried composition according to the invention is dissolved in a relatively large amount of water, this is as a rule a bath use and this use is included according to the invention in external use.

However, it is also possible to apply the freeze-dried compositions according to the invention in the dry state to the part of the body to be treated, to moisten it there with water or an aqueous solution of one or more active compounds and/or auxiliary substances or a physiological solution and to dissolve and to distribute it under gentle mechanical action, in particular by massaging.

If appropriate, gel residues remaining after the treatment can be removed from the treated part of the body by washing, wiping or rinsing off or rubbing off. This type of use is particularly preferred if the freeze-dried compositions according to the invention are used as cosmetic masks.

In therapeutic use in particular, especially in the use of the freeze-dried compositions according to the invention as a wound covering, e.g. on chronic wounds, ulcus cruris, decubitus etc., and in particular in the use of the freeze-dried compositions according to the invention for wound exudate management, the freeze-dried compositions can also be introduced in the dry state into the wound, where because of their high absorption capacity and their particular liquid uptake and storage capacity, in particular for physiological fluids, they can take up excess wound exudate or wound fluid in order thereby to assist in the healing of the wound.

In this context, as a rule the freeze-dried composition applied or introduced in the dry state into a wound to be treated is rehydrated in the wound by the body or wound fluids present, and in the course of the further treatment is either absorbed completely into the wound or washed out again with the wound fluid or other wound treatment liquids.

The present invention also relates to a combination comprising at least one of the freeze-dried compositions according to the invention or cut-out pieces thereof and at least one aqueous solution which contains one or more active compounds and/or at least one or more auxiliary substances (a so-called activator solution) in a combined spatial arrangement (use pack, set, kit-of-parts etc.).

The active compound solution or activator solution can be e.g. solutions of highly volatile active compounds and/or auxiliary substances which, because of the preparation process by freeze drying, are not to be or cannot be introduced into the freeze-dried composition, such as e.g. certain contents of essential oils, perfumes etc. They can also contain those active compounds and/or auxiliary substances which achieve a moistening action, which is desirable and preferred in particular in external use on the skin, and which because of this moistening action or because of tendencies toward hygroscopy cannot be incorporated or can be incorporated only in small amounts into the freeze-dried compositions according to the invention, since the stability of any moisture-labile active compounds contained therein can no longer be maintained. The use of physiological solutions is also preferred, since by means of such solutions it is possible to introduce into the rehydrated composition electrolytes which, because of the abovementioned polymer properties, cannot be introduced or can be introduced to only a limited extent into the polymer mixtures to be freeze-dried.

In this context, in the configuration of such kit-of-parts combinations of freeze-dried composition according to the invention on the one hand and active compound solution on the other hand the two constituents can be removed separately from the kit-of-parts arrangement and be brought together and dissolved outside of this for further use. However, it is also conceivable that the two components are brought together within the kit-of-parts package itself and the rehydrated composition is then put to the further cosmetic or pharmaceutical external or transdermal use directly from this. This can preferably be carried out directly by the end user.

The freeze-dried compositions according to the invention comprise $\geq 5$ wt. %, preferably $\geq 10$ wt. %, still more preferably $\geq 15$ wt. % of one or more polymers based on polyacrylic acids and salts thereof in the dry end product. Those chosen from the group of carbomers are particularly preferred.

The freeze-dried compositions according to the invention furthermore comprise $\geq 25$ wt. %, preferably $\geq 40$ wt. %, still more preferably a $\geq 50$ wt. % of one or more natural polymers in the dry end product. Those chosen from the group of anionic natural polymers, in particular from the group of hydrocolloid-forming polysaccharides, such as, in particular, from the group of alginates, are particularly preferred.

The freeze-dried compositions according to the invention moreover furthermore comprise $\geq 5$ wt. %, preferably $\geq 10$ wt. %, still more preferably $\geq 15$ wt. % of one or more further polymers which differ from those mentioned above. Such further polymers from the group of carrageens or from the group of mucopolysaccharides, such as hyaluronic acid, or from the collagen are particularly preferred.

The freeze-dried compositions according to the invention furthermore comprise $\geq 0.5$ wt. %, preferably $\geq 2.0$ wt. %, still more preferably $\geq 5.0$ wt. % of one or more active compounds. Such active compounds are particularly preferably chosen from the group of ascorbic acid and its derivatives, such as, in particular, ascorbyl glucoside and/or magnesium ascorbyl phosphate.

It is also possible for the freeze-dried compositions according to the invention to comprise $\geq 5$ wt. %, preferably $\geq 10$ wt. %, still more preferably $\geq 20$ wt. % of one or more optionally further auxiliary substances.

From the group of auxiliary substances, those chosen from the group of cosmetic oils, such as triglycerides, in particular caprylic/caproic acid triglycerides (neutral oil), jojoba oil or squalane, and from the group of fillers, particularly preferably mannitol, are particularly preferred.

A further particularly preferred auxiliary substance is chosen from the group of pH-adjusting agents, such as aqueous solutions of triethanolamine and/or alkali metal hydroxide solutions, in particular alkali metal hydroxide solutions, aqueous solutions of potassium hydroxide being preferred in particular. Such alkalis are added to the freeze-dried compositions according to the invention to adjust the pH of the freeze-dried compositions to a pH of between 3.0 and 6.5, preferably between pH 4.0 and 6.0, more preferably between pH 4.5 and 5.5, particularly preferably pH 5.0. If the composition of polymers, active compounds and optionally auxiliary substances per se already has a pH value which is desirable according to the invention, the addition of pH-adjusting agents can of course be omitted.

The amounts stated in each case relate to the total weight of the freeze-dried composition.

The freeze-dried compositions according to the invention optionally also comprise residues of water. Since the advantages of the freeze-dried compositions according to the invention are in particular the high stability towards decay and inactivation of unstable active compounds optionally contained therein, this so-called residual water content is to be kept as low as possible. Depending on the composition, the water content in the freeze-dried compositions can be up to 15 wt. %, based on the total composition. The water content can change, as a rule increase, during storage after the preparation of the freeze-dried compositions by freeze drying. Preferably, the water content after the freeze drying is a maximum of 10 wt. %, preferably less than 5 wt. %, more preferably less than 1 wt. %.

A particularly preferred freeze-dried composition comprises:

≥15 wt. % of one or more carbomers, such as e.g. Carbopol Ultrez 20

≥50 wt. % of one or more alginates, such as e.g. sodium alginate,

≥15 wt. % of one or more further natural polymers, such as e.g. carrageen, and/or ≥2.5 wt. % of hyaluronic acid, and ≤10 wt. %, preferably ≤5 wt. %, more preferably ≤1 wt. % of water, with the proviso that a 1 percent strength by weight solution or suspension of such a freeze-dried composition in water at 20° C. has a pH of between pH 4.0 and pH 6.0 and a mass degree of swelling of from 20 to 60.

A further preferred embodiment moreover comprises ≥5.0 wt. % of one or more active compounds, in particular ascorbic acid (vitamin C) or its derivatives or salicylic acid or its derivatives, such as acetylsalicylic acid (ASA), or silver compounds, such as silver nitrate, and other active compounds customary in wound treatment, ≤20 wt. % of one or more auxiliary substances, such as, in particular, cosmetic oils, such as neutral oil, jojoba oil or squalane, with the proviso that a 1 percent strength by weight solution or suspension of such a freeze-dried composition in water at 20° C. has a pH of between pH 4.0 and pH 6.0 and a mass degree of swelling of from 20 to 100.

A more preferred freeze-dried composition comprises:

≥5 wt. % of one or more carbomers, such as e.g. Carbopol Ultrez 20

≥15 wt. % of one or more alginates, such as e.g. sodium alginate,

≥2 wt. % of hyaluronic acid, and/or

≥5 wt. % of one or more further natural polymers, such as e.g. carrageen, and

≤10 wt. %, preferably g≤5 wt. %, more preferably ≤1 wt. % of water, with the proviso that a 1 percent strength by weight solution or suspension of such a freeze-dried composition in water at 20° C. has a pH of between pH 4.0 and pH 6.0 and a mass degree of swelling of from 20 to 60.

A further preferred embodiment moreover comprises ≥1.0 wt. % of one or more active compounds, in particular ascorbic acid (vitamin C) or its derivatives or salicylic acid or its derivatives, such as acetylsalicylic acid (ASA), or silver compounds, such as silver nitrate, and other active compounds customary in wound treatment, ≤30 wt. % of one or more auxiliary substances, such as, in particular, cosmetic oils, such as neutral oil, jojoba oil or squalane, with the proviso that a 1 percent strength by weight solution or suspension of such a freeze-dried composition in water at 20° C. has a pH of between pH 4.0 and pH 6.0 and a mass degree of swelling of from 20 to 100.

Preferably, a freeze-dried composition according to the invention, such as e.g. one of the abovementioned compositions, has a pH of between 4.0 and 6.0, preferably between pH 4.5 and pH 5.5 and particularly preferably pH 5.0, measured in a 1 wt. % solution or suspension thereof in water at 20° C., a density of from 0.005 g/cm$^3$ up to 0.8 g/cm$^3$, preferably 0.01 g/cm$^3$ up to 0.8 g/cm$^3$, an area of from 0.1 cm$^2$ to 600 cm$^2$, preferably 5 cm$^2$ to 300 cm$^2$, a thickness (shortest distance between two points of the composition) of ≥0.5 mm and/or preferably has a planar configuration, particularly preferably the form of a sheet, a pad, a covering or a mask.

The freeze-dried compositions according to the invention are porous formulations with a homogeneous distribution of the constituents.

The speed of dissolving or rehydration of the freeze-dried compositions according to the invention is ≤20 seconds, still more preferably ≤10 seconds. The measurement is performed on freeze-dried compositions according to the invention having a thickness of 1.1-1.5 mm, an area of 16 cm$^2$ and/or a weight of 0.6 g. In this context, complete hydration exists if a homogeneous gel formation without detectable inhomogeneous regions having an area of >0.1 cm$^2$ exists.

In particular, for determination of the speed of wetting, the time required by a defined sample of material to become completely and uniformly moistened through with a defined amount of liquid is determined. In this context, it is to be ensured that the moistening liquid is present in excess, so that complete wetting or moistening through is possible. Preferably, samples of material of 4×4 cm area (16 cm$^2$) and a layer thickness of 1.1-1.5 mm are also employed for this and are introduced into 7.5 ml of the moistening liquid, such as e.g. water, or into a physiological liquid, such as 0.9% strength saline solution, and the time taken for complete wetting or for complete and uniform moistening through is measured. Complete moistening through or wetting can as a rule easily be recognized from the change in colour, since the moistened regions appear darker than regions which are not yet moistened.

The speed of wetting of the freeze-dried compositions according to the invention is likewise preferably ≤20 seconds, more preferably ≤10 seconds, and still more preferably ≤5 seconds, very particularly preferably <1 second.

The invention includes in particular the following preferred embodiments:

1. Freeze-dried composition comprising
   a. at least one polymer based on polyacrylic acids and salts thereof,
   b. at least one natural polymer,
   c. optionally at least one further polymer which differs from a) and b) and
   d. optionally one or more active compounds and/or auxiliary substances.
2. Freeze-dried composition according to embodiment 1, which has an optical density of a ≥0.02 per 1 mm layer thickness of the freeze-dried composition.

3. Freeze-dried composition according to embodiment 1 or 2, the 1 percent strength by weight solution or suspension of which in water at 20° C. has a pH of from 3.0 to 6.5.
4. Freeze-dried composition according to one of embodiments 1 to 3, which has a planar form, preferably in particular the form of a sheet, a covering or a mask.
5. Freeze-dried composition according to one of embodiments 1 to 4, having a thickness of from 0.5 to 20 mm.
6. Freeze-dried composition according to one of embodiments 1 to 5, which is not chemically crosslinked.
7. Freeze-dried composition according to one of embodiments 1 to 6, which contains no textile fibre constituents,
8. Freeze-dried composition according to one of embodiments 1 to 7, which has no additional carrier layer.
9. Process for the preparation of a freeze-dried composition, comprising the steps
   a. preparation of an aqueous suspension or a solution of at least one natural polymer
   b. optionally mixing in of at least one further polymer which differs from the polymer used in step a) or e)
   c. optionally mixing in of one or more active compounds and/or auxiliary substances.
   d. adjustment of the pH of the aqueous suspension or solution to a pH of from pH 3.0 to pH 6.5
   e. preparation of an aqueous suspension or a solution of a polymer based on polyacrylic acids and salts thereof and adjustment of the pH of the solution to a pH of between pH 3.0 and pH 6.5 with alkalis
   f. combining of the suspensions or solutions prepared under a)-d) and under e) and if appropriate adjustment of the pH to pH 3.0 to 6.5
   g. pouring or spreading out of the mixture into a suitable mould or on to a suitable surface
   h. freezing of the mixture and
   i. freeze drying of the mixture to form the freeze-dried composition.
10. Process according to embodiment 9, wherein in step d), e) and f) the pH is adjusted to pH 4.5 to 5.5.
11. Process according to one of embodiments 9 to 10, wherein the adjustment of the pH is carried out by addition of inorganic alkalis, preferably a potassium hydroxide solution.
12. Process according to one of embodiments 9 to 11, wherein after step i) the freeze-dried composition is brought into a desired form, preferably a sheet, covering or mask form, by cutting.
13. Process according to embodiment 12, wherein the cut compositions have a thickness of from 0.5 to 20 mm.
14. Freeze-dried composition obtainable by the process according to one of embodiments 9 to 13.
15. Freeze-dried composition according to one of embodiments 1 to 8 or 14, wherein at least one polymer based on polyacrylic acids and salts thereof is chosen from the group of carbomers.
16. Freeze-dried composition according to one of embodiments 1 to 8 or 14 to 15, wherein at least one natural polymer is chosen from the group of polysaccharides, polyaminosaccharides and/or glucosaminoglycans.
17. Freeze-dried composition according to one of embodiments 1 to 8 or 14 to 16, wherein at least one natural polymer is chosen from the group of anionic hydrocolloids.
18. Freeze-dried composition according to embodiment 16 or 17, wherein at least one natural polymer is chosen from the group of alginates, preferably from the group of sodium alginates.
19. Freeze-dried composition according to one of embodiments 1 to 8 and 14 to 18, wherein at least one further natural polymer is chosen from the group of carrageenan and its derivatives, hyaluronic acid and its derivatives and/or collagen and its derivatives,
20. Freeze-dried composition according to one of embodiments 1 to 8 and 14 to 19, wherein at least one natural polymer is chosen from the group of alginates, preferably from the group of sodium alginates, and a further natural polymer is chosen from the group of hyaluronic acid and its derivatives.
21. Freeze-dried composition according to one of embodiments 1 to 8 and 14 to 20, wherein at least one natural polymer is chosen from the group of alginates, preferably from the group of sodium alginates, and a further natural polymer is chosen from the group of hyaluronic acid and its derivatives, and wherein it comprises at least one further polymer chosen from the group of carrageens.
22. Freeze-dried composition according to one of embodiments 1 to 8 and 14 to 21, wherein it comprises at least one further polymer, preferably chosen from the group of modified celluloses, preferably carboxymethylcellulose, particularly preferably sodium carboxymethylcellulose.
23. Freeze-dried composition according to one of embodiments 1 to 8 and 14 to 22, wherein it comprises at least one active compound from the group of cosmetic active compounds, such as, preferably, ascorbic acid or its derivatives, preferably ascorbyl glucoside or magnesium ascorbyl phosphate,
24. Freeze-dried composition according to one of embodiments 1 to 8 and 14 to 22, wherein it comprises at least one active compound from the group of therapeutic active compounds, such as, preferably, those for treatment of skin diseases and/or for wound treatment.
25. Freeze-dried composition according to one of embodiments 1 to 8 and 14 to 24, wherein it comprises at least one auxiliary substance from the group of cosmetic oils, preferably triglycerides, particularly preferably caprylic/caproic acid triglycerides and/or squalane and/or jojoba oil.
26. Freeze-dried composition according to one of embodiments 1 to 8 and 14 to 25, wherein it comprises at least one auxiliary substance from the group of fillers, particularly preferably mannitol.
27. Freeze-dried composition according to one of embodiments 1 to 8 and 14 to 26, which can be rehydrated when hydrophilic liquids are supplied, to form a homogeneous, finely disperse gel which is substantially free from macroscopic particles or fibre constituents having a size of >5 mm.
28. Freeze-dried composition according to one of embodiments 1 to 8 and 14 to 27, which has a water uptake capacity, represented as the mass degree of swelling, of from 20 to 100.
29. Freeze-dried composition according to one of embodiments 1 to 8 and 14 to 28, which forms a homogeneous, finely disperse gel having a viscosity of 10-75 mPas on addition of 96.5 g of water to 3.5 g of the freeze-dried composition at a temperature of 15-25° C. and a pH of 4.8-5.2.

30. Use of the freeze-dried composition according to one of embodiments 1 to 8 and 14 to 29 as a cosmetic agent.
31. Use according to embodiment 30 as a cosmetic covering, such as a cosmetic mask.
32. Use of the freeze-dried composition according to one of embodiments 1 to 8 and 14 to 29 as a pharmaceutical agent.
33. Use of the freeze-dried composition according to one of embodiments 1 to 8 and 14 to 29 as a wound covering.
34. Use of a freeze-dried composition according to one of embodiments 1 to 8 and 14 to 29 for the preparation of a pharmaceutical agent for wound treatment.
35. Use of a freeze-dried composition according to one of embodiments 1 to 8 and 14 to 29 for the preparation of a pharmaceutical agent for treatment of chronic wounds, such as e.g. ulcus cruris, decubitus.
36. Freeze-dried composition according to one of embodiments 1 to 8 and 14 to 29 for use as a wound covering.
37. Use according to one of embodiments 30 to 35, wherein the freeze-dried composition is applied to the part of the body to be treated, is moistened there with water or an aqueous solution of one or more active compounds and/or optionally auxiliary substances, and is disintegrated completely and distributed by mechanical action and/or massaging.
38. Use according to one of embodiments 33 to 36, wherein the freeze-dried composition is applied in the dry state to the part of the body to be treated or to the wound to be treated, where it is rehydrated by the body fluids present and in the course of the further treatment is either absorbed completely or washed out with the wound fluid or other wound treatment liquids.
39. Kit-of-parts combination comprising at least one freeze-dried composition according to one of embodiments 1 to 8 and 14 to 29 and at least one aqueous solution which contains one or more active compounds and/or optionally one or more auxiliary substances, in a combined spatial arrangement.
40. Use of the kit-of-parts combination according to embodiment 39 as a cosmetic agent.
41. Use of the kit-of-parts combination according to embodiment 39 as a therapeutic agent.
42. Use according to one of the preceding embodiments, which is carried out directly by the and user.

The invention is illustrated in more detail by the following examples.

EXAMPLES

Example 1

| | |
|---|---|
| 10.5 g | sodium carboxymethylcellulose (CMC) |
| 10.5 g | sodium alginate |
| 7.5 g | carbomer |
| 1,500 ml | RO water | a) Preparation of the Carbomer Premix 7.5 g of carbomer are dissolved in 750 ml of RO water according to the manufacturer's instructions.

b) Preparation of the Alginate/CMC Premix 10.5 g of carboxymethylcellulose and 10.5 g of sodium alginate are dissolved homogeneously in 750 ml of RO water while stirring, until no further undissolved alginate/CMC particles are visible.

c) Preparation of the Entire Batch

The carbomer premix from step a) is combined with the alginate/CMC premix from step b) by stirring until a homogeneous mixture is formed. The pH of the combined mixture is adjusted to a pH of 5.0-5.5 with dilute potassium hydroxide solution.

d) Freezing

The alginate/CMC/carbomer batch prepared in c) is frozen either by blowing cold air on to it or by application to a cold plate at temperatures of <−20° C.

e) Freeze Drying

The freeze drying of the frozen shaped body produced under d) is carried out in accordance with the prior art by generally known freeze drying processes.

f) Dividing and Assembling

The freeze-dried composition is cut into thin layers with a layer thickness of 0.5 mm. The layers are optically dense and the material can be wetted completely in less than 10 seconds.

Example 2

| | |
|---|---|
| 7.5 g | sodium carboxymethylcellulose (CMC) |
| 4.5 g | carrageenan |
| 4.5 g | carbomer |
| 4.5 g | fish collagen hydrolysate |
| 4.5 g | hyaluronic acid |
| 3.0 g | sodium alginate |
| 7.5 g | calcium alginate |
| 15.0 g | mannitol |
| 1,500 ml | RO water | a) Preparation of the Carbomer Premix 4.5 g of carbomer are dissolved in 500 ml of RO water according to the manufacturer's instructions.

b) Preparation of the Alginate/CMC/Hyaluronic Acid/Mannitol/Fish Collagen Hydrolysate Premix The remaining substances are dissolved hot in 1,000 ml of RO water, until undissolved substances are no longer detectable. The solution is then allowed to cool to room temperature.

c) Preparation of the Entire Batch

The carbomer premix from step a) is combined with the premix from step b) by stirring until a homogeneous mixture is formed. The pH of the combined mixture is adjusted to a pH of 5.0-5.5 with dilute potassium hydroxide solution.

d) Freezing

The batch prepared in c) is frozen either by blowing cold air on to it or by application to a cold plate at temperatures of <−20° C.

e) Freeze Drying

The freeze drying of the frozen shaped body produced under d) is carried out in accordance with the prior art by generally known freeze drying processes.

f) Dividing and Assembling

The freeze-dried composition is cut into thin layers with a layer thickness of 1.5 mm. The layers are optically dense and the material can be wetted completely in less than 10 seconds.

Example 3

| | |
|---|---|
| 7.5 g | sodium alginate |
| 4.5 g | carrageenan |
| 11.25 g | carbomer |
| 1,500 ml | RO water | a) Preparation of the Carbomer Premix 11.25 g of carbomer are dissolved in 750 ml of RO water according to the manufacturer's instructions.

b) Preparation of the Alginate/Carrageenan Premix 7.5 g of Na alginate and 4.5 g of carrageenan are dissolved homogeneously in 750 ml of hot RO water while stirring, until no further undissolved particles are visible.

c) Preparation of the Entire Batch

The carbomer premix from step a) is combined with the alginate/carrageenan premix from step b) by stirring until a homogeneous mixture is formed. The pH of the combined mixture is adjusted to a pH of 5.0 with dilute potassium hydroxide solution.

d) Freezing

The alginate/carrageenan/carbomer batch prepared in c) is frozen either by blowing cold air on to it or by application to a cold plate at temperatures of <–20° C.

e) Freeze Drying

The freeze drying of the frozen shaped body produced under d) is carried out in accordance with the prior art by generally known freeze drying processes.

f) Dividing and Assembling

The freeze-dried composition is out into thin layers with a layer thickness of 2.0 mm. The layers are optically dense and the material can be wetted completely in >30 seconds.

Example 4

| | |
|---|---|
| 10.5 g | sodium carboxymethylcellulose (CMC) |
| 10.5 g | sodium alginate |
| 7.5 g | carbomer |
| 1.5 g | hyaluronic acid |
| 1,500 ml | RO water | a) Preparation of the Carbomer Premix 7.5 g of carbomer are dissolved in 750 ml of RO water according to the manufacturer's instructions.

b) Preparation of the Alginate/Hyaluronic Acid/CMC Premix 10.5 g of carboxymethylcellulose, 1.5 g of hyaluronic acid and 10.5 g of sodium alginate are dissolved homogeneously in 750 ml of RO water while stirring, until no further undissolved alginate/hyaluronic acid/CMC particles are visible.

c) Preparation of the Entire Batch

The carbomer premix from step a) is combined with the alginate/hyaluronic acid/CMC premix from step b) by stirring until a homogeneous mixture is formed. The pH of the combined mixture is adjusted to a pH of 5.0-5.5 with dilute potassium hydroxide solution.

d) Freezing

The alginate/hyaluronic acid/CMC/carbomer batch prepared in c) is frozen either by blowing cold air on to it or by application to a cold plate at temperatures of <–20° C.

e) Freeze Drying

The freeze drying of the frozen shaped body produced under d) is carried out in accordance with the prior art by generally known freeze drying processes.

f) Dividing and Assembling

The freeze-dried composition is out into thin layers with a layer thickness of 0.5 mm. The layers are optically dense and the material can be wetted completely in less than 5 seconds.

Example 5

| | |
|---|---|
| 3.0 g | sodium carboxymethylcellulose (CMC) |
| 4.5 g | carrageenan |
| 4.5 g | carbomer |
| 4.5 g | fish collagen hydrolysate |
| 1.5 g | hyaluronic acid |
| 7.5 g | sodium alginate |
| 1,500 ml | RO water | a) Preparation of the Carbomer Premix 4.5 g of carbomer are dissolved in 500 ml of RO water according to the manufacturer's instructions.

b) Preparation of the Alginate/CMC/Carrageen/Hyaluronic Acid/Fish Collagen Hydrolysate Premix The remaining substances are dissolved hot in 1,000 ml of RO water, until undissolved substances are no longer detectable. The solution is then allowed to cool to room temperature.

c) Preparation of the Entire Batch

The carbomer premix from step a) is combined with the premix from step b) by stirring until a homogeneous mixture is formed. The pH of the combined mixture is adjusted to a pH of 5.0-5.5 with dilute potassium hydroxide solution.

d) Freezing

The batch prepared in c) is frozen either by blowing cold air on to it or by application to a cold plate at temperatures of <–20° C.

e) Freeze Drying

The freeze drying of the frozen shaped body produced under d) is carried out in accordance with the prior an by generally known freeze drying processes.

f) Dividing and Assembling

The freeze-dried composition is cut into thin layers with a layer thickness of 1.5 mm. The layers are optically dense and the material can be wetted completely in less than 1 second.

Example 6

| | |
|---|---|
| 11.25 g | sodium alginate |
| 4.5 g | carrageenan |
| 11.25 g | carbomer |
| 1.5 g | hyaluronic acid |
| 7.5 g | sodium carboxymethylcellulose (CMC) |
| 7.5 g | mannitol |
| 1,500 ml | RO water | a) Preparation of the Carbomer Premix 11.25 g of carbomer are dissolved in 750 ml of RO water according to the manufacturer's instructions.

b) Preparation of the Alginate/Hyaluronic Acid/Carrageenan/CMC/Mannitol Premix

The remaining substances are dissolved in 750 ml of hot RO water, until no further undissolved particles are visible. The solution is then allowed to cool to room temperature.

c) Preparation of the Entire Batch

The carbomer premix from step a) is combined with the alginate/hyaluronic acid/carrageenan/CMC mannitol premix from step b) by stirring until a homogeneous mixture is formed. The pH of the combined mixture is adjusted to a pH of 5.0 with dilute potassium hydroxide solution.

d) Freezing

The batch prepared in c) is frozen either by blowing cold air on to it or by application to a cold plate at temperatures of <−20° C.

e) Freeze Drying

The freeze drying of the frozen shaped body produced under d) is carried out in accordance with the prior art by generally known freeze drying processes.

f) Dividing and Assembling

The freeze-dried composition is cut into thin layers with a layer thickness of 2.0 mm. The layers are optically dense and the material can be wetted completely in less than 1 second.

Example 7

| | |
|---|---|
| 7.5 g | sodium carboxymethylcellulose (CMC) |
| 4.5 g | carrageenan |
| 11.25 g | carbomer |
| 1.5 g | hyaluronic acid |
| 11.25 g | sodium alginate |
| 7.5 g | mannitol |
| 1.5 g | jojoba oil |
| 0.75 g | magnesium ascorbyl phosphate |
| 1,500 ml | RO water | a) Preparation of the Carbomer Premix 11.25 g of carbomer are dissolved in 700 ml of RO water according to the manufacturer's instructions.

b) Preparation of the Alginate/Hyaluronic Acid/Carrageenan/CMC/Mannitol/Jojoba Oil Premix The remaining substances, apart from the jojoba oil and the magnesium ascorbyl phosphate, are dissolved in 750 ml of hot RO water, until no further undissolved particles are visible. The solution is then allowed to cool to room temperature. The jojoba oil is then mixed in.

c) Preparation of the Magnesium Ascorbyl Phosphate Premix

The 0.75 g of magnesium ascorbyl phosphate are dissolved in 50 ml of RO water until no further undissolved particles are visible.

d) Preparation of the Entire Batch

The carbomer premix from step a) is combined with the alginate/hyaluronic acid/carrageenan/CMC mannitol/jojoba oil premix from step b) by stirring until a homogeneous mixture is formed. The active compound solution from step c) is likewise mixed in homogeneously by stirring. The pH of the combined mixture is then adjusted to a pH of 5.0 with dilute potassium hydroxide solution.

e) Freezing

The batch prepared in d) is frozen either by blowing cold air on to it or by application to a cold plate at temperatures of <−20° C.

f) Freeze Drying

The freeze drying of the frozen shaped body produced under e) is carried out in accordance with the prior art by generally known freeze drying processes.

g) Dividing and Assembling

The freeze-dried composition is cut into thin layers with a layer thickness of 2.0 mm. The layers are optically dense and the material can be wetted completely in less than 1 second.

Example 8

The influence of the structure-forming polymers and various possible combinations thereof in freeze-dried sheet-like compositions in the context of the present invention was investigated with the aid of the speed of wetting and the liquid retention capacity.

In this context, the investigations were conducted on compositions which comprise only one of the structure-forming polymers carbomer, alginate, hyaluronic acid or carrageen, compositions with a combination of two of these structure-forming polymers, such as e.g. are also known from the prior art, and the compositions which are preferred according to the invention, which comprise a combination of the three structure-forming polymers carbomer, alginate and hyaluronic acid. A further preferred composition which furthermore comprises carrageen in addition to these three polymers was moreover investigated.

For this, if possible according to the preparation, the speed of wetting and the liquid retention capacity was determined with the mass swelling index $Q_M$ and the volume of liquid held per gram of composition. The experiments were carried out by the methods described above under the experimental conditions stated there.

All the experiments were carried out both with water and with a physiological saline solution (0.9% strength NaCl solution).

The results are summarized in the following tables, with the following meanings for the notes:

at a high DM (dry matter) too viscous or gelling at <40° C. not pumpable, at a low DM unstable in the frozen state mechanically not stable to cutting; this can mean either that the structure of the matrix is too open-pored and crumbles during cutting, or that from the beginning no cohesive cuttable matrix exists, but only fibres laid loosely on one another which are squashed by the blade during cutting and are not cut.

expensive

Speed of Wetting:

Compositions with One Structure-Forming Polymer

| Example | Polymer | Processability | Speed of wetting in water | Speed of wetting in 0.9% strength NaCl soln. |
|---|---|---|---|---|
| | carbomer | cannot be prepared (*/**) | cannot be measured | cannot be measured |
| | alginate | cannot be prepared (**) | cannot be measured | cannot be measured |

-continued

| Example | Polymer | Processability | Speed of wetting in water | Speed of wetting in 0.9% strength NaCl soln. |
|---|---|---|---|---|
| | hyaluronic acid | cannot be prepared (/*) | cannot be measured | cannot be measured |
| | carrageenan | cannot be prepared (*/**) | cannot be measured | cannot be measured |

Compositions with Two Structure-Forming Polymers

| Example | Polymers | Processability | Speed of wetting in water | Speed of wetting in 0.9% strength NaCl soln. |
|---|---|---|---|---|
| prior art | carbomer + alginate | poor (**) | disintegrates into small pieces | disintegrates into small pieces |
| prior art | carbomer + hyaluronic acid | cannot be prepared (*//*) | cannot be measured | cannot be measured |
| | carbomer + carrageenan | cannot be prepared (*) | cannot be measured | cannot be measured |
| | alginate + hyaluronic acid | cannot be prepared (**) | cannot be measured | cannot be measured |
| | alginate + carrageenan | cannot be prepared (**) | cannot be measured | cannot be measured |
| | hyaluronic acid + carrageenan | cannot be prepared (*/***) | cannot be measured | cannot be measured |

Compositions with at Least Three Structure-Forming Polymers

| Example | Polymers | Processability | Speed of wetting in water | Speed of wetting in 0.9% strength NaCl soln. |
|---|---|---|---|---|
| 4 | carbomer + alginate + hyaluronic acid | good | <5 seconds | <5 seconds |
| 3 | carbomer + alginate + carrageenan | good | >30 seconds | >30 seconds |
| | carbomer + hyaluronic acid + carrageenan | good | >10 seconds | >10 seconds |
| | alginate + hyaluronic acid + carrageenan | good | >60 seconds | >60 seconds |
| 5, 6, 7 | carbomer + alginate + hyaluronic acid + carrageenan | good | ≤1 second | ≤1 second |

Liquid Uptake/Retention Capacity:

Experiments on the liquid uptake or retention capacity were carried out with compositions which comprise at least three structure-forming polymers, the results of which are as shown below:

| Example | Polymers | Ø water ml/g | Ø 0.9% strength NaCl soln. ml/g | Ø $Q_M$ in water | Ø $Q_M$ in 0.9% strength NaCl soln. | Ø $\Delta Q_M$ |
|---|---|---|---|---|---|---|
| 4 | carbomer + alginate + hyaluronic acid | 35 | 33 | 36 | 34 | 2 |
| 3 | carbomer + alginate + carrageenan | 48 | 30 | 49 | 31 | 18 |
|   | carbomer + hyaluronic acid + carrageenan | 61 | 28 | 62 | 29 | 33 |
|   | alginate + hyaluronic acid + carrageenan | 23 | 19 | 24 | 20 | 4 |
| 5, 6, 7 | carbomer + alginate + hyaluronic acid + carrageenan | 35 | 28 | 36 | 29 | 7 |

It was found during the preparation of the various matrices that compositions which comprised only one polymer either could not be processed in the liquid/viscous state, or were not able to show a sufficient mechanical stability in the freeze-dried state for preparation of cut sheets or pads.

Similar problems during preparation were found from the group of compositions with a combination of two polymers. It was indeed possible to obtain sheet-like compositions here with a carbomer/alginate combination, but these likewise showed a decidedly poor mechanical stability in the application or in contact with liquid, in that they disintegrated into small pieces.

Mechanically stable, sheet-like materials were to be obtained only from compositions with a combination of at least three of the structure-forming polymers.

Clear differences were found with respect to the wetting and liquid retention properties of these materials.

Exclusively compositions which comprise a combination of carbomer, alginate and hyaluronic acid have sufficiently high speeds of wetting. For the other possible combinations, it was indeed possible now to obtain mechanically stable compositions, but these showed clearly disadvantageous speeds of wetting of from >10 to >60 seconds and therefore extremely poor liquid uptake properties.

It was furthermore found that the decidedly good wetting and the liquid uptake properties of compositions with carbomer, alginate and hyaluronic acid can be improved still further by the addition of carrageen.

In this context, however, the experiments also show that the nature of the alginate used has an influence on the wetting properties. A comparison of Example 2, in which carbomer and hyaluronic acid were combined with sodium alginate and calcium alginate, with Example 5, in which a comparable composition exclusively with sodium alginate is shown, illustrates this influence. Ca ions are known to have alginate-crosslinking properties, which is reflected in a disadvantageous manner in the wetting or dissolving of the compositions. Thus, compositions according to Example 2 have higher speeds of wetting, with <10 seconds, than those according to Example 5, which contain no Ca alginate and have a speed of wetting of <1 second.

It thus emerges from this that only compositions which comprise a combination of carbomer, alginate, particularly preferably sodium alginate, and hyaluronic acid achieve the speeds of wetting which are preferred according to the invention, of <10, more preferably of <5, still more preferably <1 second.

The results furthermore show that compositions which comprise a combination of carbomer, alginate and hyaluronic acid have a better capacity for storage of physiological fluids. In particular, it was found in this context that the liquid retention capacity of compositions with carbomer, alginate and hyaluronic acid was consistently good and could be kept stable in the comparison of the storage of pure water to the storage of physiological fluids, which is clear in particular from the significantly lower decrease in the mass swelling index ($\Delta Q_M$) in the comparison of these values. A similarly stable liquid retention capacity was shown only by compositions of alginate, hyaluronic acid and carrageen (without carbomer), such compositions also showing the poorest absolute liquid retention capacity, in addition to an extremely poor speed of wetting.

Summarizing, it can be said that among the polymer combinations investigated, only the compositions which comprise a combination of carbomer, alginate and hyaluronic acid have the combination desired according to the invention of very good liquid uptake and speed of wetting of <10 seconds and a high liquid retention capacity which is also stable in electrolyte-containing liquids.

The invention claimed is:

1. A pad for topical application consisting of a mechanically stable, cohesive, freeze-dried composition comprising
    a) ≥10 wt % of at least one hydrocolloid polymer, wherein the hydrocolloid polymer is a polyacrylate, a synthetic acrylic polymer or a salt thereof,
    b) ≥40 wt % of one natural polymer, wherein the natural polymer is an anionic natural hydrocolloid,
    c) at least two further natural polymers which differ from a) and b); and wherein the at least one of the at least two further natural polymers is carrageenan, a carrageenan derivative, hyaluronic acid, a hyaluronic acid derivative, collagen or a collagen derivative, and
    d) one or more active compounds and/or auxiliary substances, wherein at least one auxiliary substance is caprylic/caproic acid, jojoba oil or squalane;
    wherein a 1 percent by weight solution or suspension of the freeze-dried composition comprising components (a), (b) and (c) in water at 20° C. has a pH of from 3.0 to 6.5.

2. The pad according to claim 1, which has an optical density of ≥0.02 per 1 mm layer thickness of the freeze-dried composition.

3. The pad according to claim 1, which is neither ionically nor chemically crosslinked and which contains no textile fibre constituents and no additional carrier layers.

4. The pad according to claim 1, wherein at least one hydrocolloid polymer a) is chosen from the group of carbomers.

5. The pad according to claim 1, wherein the anionic natural hydrocolloid polymer b) is chosen from the group of polysaccharides, polyaminosaccharides and glucosaminoglycans.

6. The pad according to claim 5, wherein the anionic natural hydrocolloid polymer b) is chosen from the group of hyaluronic acid and its derivatives.

7. The pad according to claim 1, wherein it comprises at least one auxiliary substance selected from cosmetic oils.

8. A kit-of-parts combination comprising at least one pad according to claim 1 and at least one aqueous solution which contains one or more active compounds and/or optionally one or more auxiliary substances, with the pad and the aqueous solution being arranged in a combined spatial arrangement.

9. The pad according to claim 5, wherein the polysaccharide is chosen from the group of alginates, carrageen, pectins, pullulan, tragacanth, guar gum, carob bean flour, agar-agar, gum arabic, xanthan, natural and modified starches, dextrans, dextrin, maltodextrins, chitosan, glucans, mucopolysaccharides.

10. The pad according to claim 1, which has a thickness of 0.5 to 20 mm.

11. A pad for topical application consisting of a mechanically stable, cohesive, freeze-dried composition consisting of
   a) one hydrocolloid polymer, wherein the hydrocolloid polymer is a polyacrylate, synthetic acrylic polymer or thereof, in the amount of at least 5 percent by weight of the total composition,
   b) at least one natural polymer, wherein the natural polymer is an anionic natural hydrocolloid, in the amount of at least 25 percent by weight of the total composition,
   c) one or more active compounds and/or auxiliary substances, wherein at least one auxiliary substance is caprylic/caproic acid, jojoba oil or squalane, and
   d) at least two further natural polymers which differ from a) and b); wherein the at least one of the at least two further natural polymers is carrageenan, a carrageenan derivative, hyaluronic acid, a hyaluronic acid derivative, collagen, or a collagen derivative, and
   wherein a solution or suspension of the freeze-dried composition comprising components (a), (b), (c) and (d) in the amount of 1 percent by weight of the total weight of the solution or suspension in water at 20° C. has a pH of from 3.0 to 6.5.

12. The pad according to claim 11, wherein the anionic natural hydrocolloid b) is selected from the group of glucosaminoglycans, hyaluronic acid and its derivatives.

13. The pad according to claim 1, wherein the pad does not comprise cellulose.

14. The pad according to claim 11, wherein the pad does not comprise cellulose.

\* \* \* \* \*